US008785355B2

(12) United States Patent
Hartshorne et al.

(10) Patent No.: US 8,785,355 B2
(45) Date of Patent: Jul. 22, 2014

(54) VISCOELASTIC COMPOSITIONS

(75) Inventors: Robert Seth Hartshorne, Newmarket (GB); Trevor Lloyd Hughes, Cambridge (GB); Timothy Gareth John Jones, Cottenham (GB); Gary John Tustin, Sawston (GB); Jian Zhou, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 557 days.

(21) Appl. No.: 12/466,411

(22) Filed: May 15, 2009

(65) Prior Publication Data

US 2009/0291864 A1    Nov. 26, 2009

Related U.S. Application Data

(63) Continuation-in-part of application No. 10/993,985, filed on Nov. 19, 2004, now abandoned, which is a continuation-in-part of application No. 10/250,415, filed as application No. PCT/GB02/00587 on Feb. 12, 2002, now Pat. No. 7,704,926.

(30) Foreign Application Priority Data

Feb. 13, 2001  (GB) .................................. 0103449.5
Nov. 29, 2003  (GB) .................................. 0327795.1

(51) Int. Cl.
*C09K 8/532*    (2006.01)
(52) U.S. Cl.
USPC ........................................................ 507/259
(58) Field of Classification Search
USPC ........................................................ 507/259
See application file for complete search history.

(56) References Cited

U.S. PATENT DOCUMENTS

| | | |
|---|---|---|
| 1,932,180 A | 10/1933 | Guenther et al. |
| 1,981,792 A | 11/1934 | Orelup |
| 2,098,203 A | 11/1937 | Bruson |
| 2,106,716 A | 2/1938 | Bruson |
| 2,115,192 A | 4/1938 | Bruson |
| 2,658,072 A | 11/1953 | Kosmin |
| 2,715,108 A | 8/1955 | Francis |
| 2,775,560 A | 12/1956 | Lurton et al. |
| 2,836,560 A | 5/1958 | Teale et al. |
| 3,762,932 A | 10/1973 | Buddemeyer et al. |
| 3,886,293 A | 5/1975 | Zech |
| 3,921,716 A | 11/1975 | Tate |
| 3,921,718 A | 11/1975 | Tate |
| 3,924,685 A | 12/1975 | Tate |
| 3,995,705 A | 12/1976 | Fischer et al. |
| 4,101,425 A | 7/1978 | Young et al. |
| 4,116,986 A | 9/1978 | Bistline, Jr. et al. |
| 4,506,734 A | 3/1985 | Nolte |
| 4,695,389 A | 9/1987 | Kubala |
| 4,725,372 A | 2/1988 | Teot et al. |
| 4,735,731 A | 4/1988 | Rose et al. |
| 4,853,138 A | 8/1989 | Loza et al. |
| 5,171,476 A | 12/1992 | Bloodworth et al. |
| 5,258,137 A | 11/1993 | Bonekamp et al. |
| 5,551,516 A | 9/1996 | Norman et al. |
| 5,925,747 A | 7/1999 | Uphues et al. |
| 5,964,295 A | 10/1999 | Brown et al. |
| 5,979,555 A | 11/1999 | Gadberry et al. |
| 5,979,557 A | 11/1999 | Card et al. |
| 6,035,936 A | 3/2000 | Whalen |
| 6,194,356 B1 | 2/2001 | Jones et al. |
| 6,239,183 B1 | 5/2001 | Farmer et al. |
| 6,302,209 B1 | 10/2001 | Thompson, Sr. et al. |
| 6,306,800 B1 | 10/2001 | Samuel et al. |
| 6,399,546 B1 | 6/2002 | Chang et al. |
| 6,410,489 B1 | 6/2002 | Zhang et al. |
| 6,412,561 B1 | 7/2002 | Brown et al. |
| 6,435,277 B1 * | 8/2002 | Qu et al. .................. 166/281 |
| 6,455,483 B1 | 9/2002 | Carey |
| 6,468,945 B1 | 10/2002 | Zhang |
| 6,482,866 B1 | 11/2002 | Dahayanake et al. |
| 6,491,099 B1 | 12/2002 | Di Lullo Arias et al. |

(Continued)

FOREIGN PATENT DOCUMENTS

| | | |
|---|---|---|
| CA | 2407344 A1 | 11/2001 |
| CA | 2434357 A1 | 8/2002 |

(Continued)

OTHER PUBLICATIONS

Wikipedia A—http://en.wikipedia.org/wiki/coconut_oil (date unknown).*

(Continued)

*Primary Examiner* — Kuo-Liang Peng
(74) *Attorney, Agent, or Firm* — Jeremy D. Tillman; Rachel E. Greene; Tim Curington

(57) ABSTRACT

The present invention provides aqueous viscoelastic compositions comprising a cleavable anionic surfactant which is a sulphonate and possibly also an electrolyte. The cleavable surfactants useful in the present invention comprise a chemical bond, which is capable of being broken under appropriate conditions, to produce oil soluble and water soluble products typically having no interfacial properties and surface activity compared with the original surfactant molecule. Further, the rheological properties of the aqueous viscoelastic composition are usually altered upon cleavage of the cleavable surfactant generally resulting in the elimination of the viscosifying, viscoelastic and surfactant properties of the composition. Aqueous viscoelastic compositions in accordance with the present invention are suitable for use in oilfield applications, particularly for hydraulic fracturing of subterranean formations. Thus, the present invention also relates to a wellbore service fluid and a method of fracturing a subterranean formation.

31 Claims, 8 Drawing Sheets

(56) References Cited

U.S. PATENT DOCUMENTS

| | | | |
|---|---|---|---|
| 6,506,710 B1 | 1/2003 | Hoey et al. | |
| 6,605,570 B2 | 8/2003 | Miller et al. | |
| 6,637,517 B2 | 10/2003 | Samuel et al. | |
| 6,703,352 B2 | 3/2004 | Dahayanake et al. | |
| 6,727,196 B2 | 4/2004 | Yahiaoui et al. | |
| 6,762,154 B2 | 7/2004 | Lungwitz et al. | |
| 6,767,869 B2 | 7/2004 | DiLullo et al. | |
| 6,831,108 B2 | 12/2004 | Dahanayake et al. | |
| 6,844,297 B2 | 1/2005 | Allan et al. | |
| 6,875,728 B2 | 4/2005 | Gupta et al. | |
| 6,881,709 B2 | 4/2005 | Nelson et al. | |
| 6,908,888 B2 | 6/2005 | Lee et al. | |
| 6,920,928 B1 | 7/2005 | Davies et al. | |
| 7,036,585 B2 | 5/2006 | Zhou et al. | |
| 7,060,661 B2 | 6/2006 | Dobson, Sr. et al. | |
| 7,156,177 B2 | 1/2007 | Jones et al. | |
| 7,410,934 B2 | 8/2008 | Hughes et al. | |
| 7,670,995 B2 | 3/2010 | Hughes et al. | |
| 7,704,926 B2 | 4/2010 | Zhou et al. | |
| 2002/0023752 A1 | 2/2002 | Qu et al. | |
| 2002/0189810 A1* | 12/2002 | DiLullo et al. | 166/294 |
| 2003/0073585 A1 | 4/2003 | DiLullo Arias et al. | |
| 2004/0094301 A1* | 5/2004 | Hughes et al. | 166/308.2 |
| 2005/0124525 A1 | 6/2005 | Hartshorne et al. | |

FOREIGN PATENT DOCUMENTS

| | | |
|---|---|---|
| DE | 19539845 | 11/1996 |
| DE | 19539876 | 12/1996 |
| EP | 0232153 A2 | 8/1987 |
| EP | 0552032 A2 | 7/1993 |
| EP | 0747468 | 12/1996 |
| EP | 0747468 A1 | 12/1996 |
| EP | 835983 B1 | 12/2003 |
| GB | 2332224 | 6/1999 |
| GB | 2334277 A | 8/1999 |
| GB | 2393722 B | 4/2004 |
| GB | 2389604 B | 12/2004 |
| JP | 64090284 A | 4/1989 |
| JP | 4149169 A | 5/1992 |
| JP | 5202168 A | 8/1993 |
| JP | 2003233186 A | 8/2003 |
| WO | WO9101295 | 2/1991 |
| WO | WO9317085 | 9/1993 |
| WO | WO9325648 | 12/1993 |
| WO | WO9409852 | 5/1994 |
| WO | 9924693 A1 | 5/1999 |
| WO | 0118147 A1 | 3/2001 |
| WO | 0177487 A2 | 10/2001 |
| WO | 0211874 A1 | 2/2002 |
| WO | 02064945 A1 | 8/2002 |
| WO | 02064946 A1 | 8/2002 |
| WO | 02064947 A1 | 8/2002 |

OTHER PUBLICATIONS

Wikipedia B—http://en.wikipedia.org/wiki/Tallow (date unknown).*
Borchardt et al: "Surfactants for CO2 foam flooding", 60th Technical Conference and Exhibition of the Society of Petroleum Engineers, Las Vegas, Sep. 22-25, 1985, SPE 14394.
Butler et al: "The hydrolysis of acetic anhydride. Part VII. Catalysis by pyridine and methylpyridines in acetate buffers", Journal of the Chem. Society, 1961, pp. 4362-4367.
Chambers: "Foams for well stimulation", Foams: Fundamentals and applications in the petroleum industry, (Schramm ed.), Advances in Chemistry Series 1994, chapter 9, vol. 242, pp. 355-404.
Chang et al: "Case study of a novel acid-diversion technique in carbonate reservoirs", SPE Annual Technical Conference and Exhibition, Houston, Texas, Oct. 3-6, 1999, SPE 56529.
Fersht et al: "The acetylpyridinium ion intermediate in pyridine-catalyzed hydrolysis and acyl transfer reactions of acetic anhydride. Observation, kinetics, structure-reactivity correlations, and effects of concentrated salt solutions", Journal of the American Chemical Society, vol. 92, 1970, pp. 5432-5442.
Heller: "CO2 foams in enhanced oil recovery", Foams: Fundamentals and applications in the petroleum industry, (Schramm ed.), Advances in Chemistry Series 1994, vol. 242, chapter 5, pp. 201-234.
Holmberg: "Cleavable surfactants", Novel Surfactants (Holmberg ed.), Marcel Dekker Inc, New York, 1998, pp. 333-358.
Kaiser et al: "Synthesis of esters of acid-unstable alcohols by means of n-butyllithium", Journal of Organic Chemistry, vol. 35, No. 4, 1970, pp. 1198-1199.
Krüger et al; "Esterquats", Novel Surfactants: Preparation, Applications and Biodegradability, (Holmberg ed.), Marcel Dekker Inc, New York, 1998, pp. 115-138.
Larock: "Carboxylic acids to acid halides", Comprehensive Organic Transformations: a guide to functional group preparations, 2nd edition, 1999, Wiley-VCH, pp. 1929-1930.
Maitland: "Oil and gas production", Current Opinion in Colloid & Interface Science, vol. 5, 2000, pp. 301-311.
Porter: "Anionics", Handbook of Surfactants, 2nd Edition, Blackie Academic & Professional, Chapman & Hall, 1994, Chapter 6, particularly pp. 112-113.
Satchell: "An outline of acylation", Quarterly Reviews of the Chem. Society, vol. 17, 1963, pp. 160-203.
Smith et al: "Aliphatic nucleophilic substitution", March's Advanced Organic Chemistry, 5th edition, Wiley-Interscience, New York, 2001, pp. 482, 498-502, 506-514 and 574-578.
Smith et al: "Aromatic electrophilic substitution", March Advanced Organic Chemistry, 5th edition, Wiley- Interscience, New York, 2001, pp. 701-704.
Sommer et al: "Alkylation of amines. A general exhaustive alkylation method for the synthesis of quaternary ammonium compounds", Journal of Organic Chemistry, vol. 36, No. 6, 1971, pp. 824-828.
Sommer et al: "Alkylation of amines. A new method for the synthesis of quaternary ammonium compounds from primary and secondary amines", Journal of Organic Chemistry, vol. 35, 1970, pp. 1558-1562.
Wikipedia: "Coconut oil", article available at: http://en.wikipedia.org/wiki/coconut_oil.
Wikipedia: "Tallow", article available at: http://en.wikipedia.org/wiki/Tallow.
Yoneda et al: "A kinetic study of the reaction between sulfite ion and propylene oxide", Journal of Organic Chemistry, vol. 40, No. 3, 1975, pp. 375-377.
Per-Erik Hellberg et al., "Cleavable Surfactants," Journal of Surfactants and Detergents, Jan. 2000, vol. 3(1): pp. 81-91.
Janet Gulbis et al., "Encapsulated Breaker for Aqueous Polymeric Fluids," SPE Production Engineering, Feb. 1992: pp. 1-9.
Antti Kivinen, "Mechanisms of substitution at the COX group," The chemistry of acyl halides, Interscience Publishers, Saul Patai, editor, New York, 1972: pp. 177-230.
G. C. Maitland, "Oil and gas production," Colloid & Interface Science, Current Opinion in Colloid & Interface Science, 2000, vol. 5: pp. 301-311.
Biermann, et al., "Chapter 3: Synthesis of Surfactants," Surfactants in Consumer Products, 1987, pp. 24-132, Springer-Verlag, Heidelberg.
Lindstedt, et al., "Antimicrobial Activity of Betaine Esters, Quaternary Ammonium Amphiphiles Which Spontaneously Hydrolyze into Nontoxic Components," Antimicrobial Agents and Chemotherapy, Oct. 1990, pp. 1949-1954, vol. 34, No. 10, American Society for Microbiology.
Muzyczko, et al., "Fatty Amidoamine Derivatives: N,N-Dimethyl-N-(3-alkylamidopropyl)annines and Their Salts," Journal of the American Oil Chemists Society, pp. 720-725, Nov. 1968, vol. 45.
Raghavan, et al., "Highly Viscoelastic Wormlike Micellar Solutions Formed by Cationic Surfactants with Long Unsaturated Tails," Langmuir, 2001, pp. 300-306, vol. 17, No. 2., American Chemical Society.
Shapiro, et al., "Environmentally Friendly Ester Quats," Cosmetics & Toiletries magazine, Dec. 1994, pp. 77-80, vol. 109, Allured Publishing Corp.

* cited by examiner

40% Adinol OT64 in IPA (4%) Deionised water

VISCOELASTIC COMPOSITIONS

CROSS REFERENCE TO RELATED APPLICATIONS

This application is a continuation-in-part of U.S. patent application Ser. No. 10/250,415 filed 15 Dec. 2003 and now U.S. Pat. No. 7,704,926 which is a US national stage filing of International Application PCT/GB02/00587 filed 13 Feb. 2002 (published as WO 02/064945) which claims priority of GB patent application GB 0103449.5 filed 13 Feb. 2001. This application is also a continuation-in-part of U.S. patent application Ser. No. 10/993,985 filed 19 Nov. 2004 which claims priority from GB patent application GB 0327795.1 filed 29 Nov. 2003. The disclosures of the above mentioned U.S. Ser. Nos. 10/250,415 and 10/993,985 applications are incorporated herein by reference.

FIELD OF THE INVENTION

The present invention concerns viscoelastic compositions suitable for use in oil-field applications. These applications include, but are not limited to, hydraulic fracturing of subterranean formations.

Viscoelastic compositions are compositions having significant elastic properties such that when an applied stress is released, the composition exhibits a behaviour intermediate between the Hookean (elastic solid) and Newtonian (viscous fluid) extremes.

The present invention relates specifically to anionic viscoelastic surfactants with a sulphonate head-group and to viscoelastic wellbore treatment fluids comprising such surfactants.

BACKGROUND OF THE INVENTION

Hydrocarbons such as oil, natural gas, etc. are obtained from a subterranean geologic formation (e.g. a "reservoir") by drilling a well that penetrates the hydrocarbon-bearing formation. This provides a partial flowpath for the hydrocarbon, typically oil, to reach the surface. In order for oil to be "produced", that is, travel from the formation to the wellbore (and ultimately to the surface), there must be a sufficiently unimpeded flowpath through the formation rock (e.g. sandstone, carbonates), which generally occurs when rock pores of sufficient size and number are present.

In the recovery of hydrocarbons, such as oil and gas, from natural hydrocarbon reservoirs, extensive use is made of wellbore treatment fluids such as drilling fluids, completion fluids, workover fluids, packer fluids, fracturing fluids, conformance or permeability control fluids and the like.

Generally, techniques used to increase the permeability of the formation are referred to as "stimulation". Stimulation of the formation can be performed by: (1) injecting chemicals into the wellbore to react with and/or dissolve damage; (2) injecting chemicals through the wellbore and into the formation to react with and/or dissolve small portions of the formation to create alternative flowpaths for the hydrocarbon; or (3) injecting chemicals through the wellbore and into the formation at pressures sufficient to fracture the formation, thereby creating a channel through which hydrocarbon can more readily flow from the formation and into the wellbore.

Hydraulic fracturing involves breaking or fracturing a portion of the surrounding strata of the formation, by injecting a specialised fluid into the wellbore directed at the face of the formation at pressures sufficient to initiate and extend a fracture in the formation. Typically, the process creates a fracture zone, that is, a zone in the formation having multiple fractures, through which hydrocarbon can more easily flow to the wellbore.

In many cases significant components of fracturing fluids and other wellbore fluids are thickening agents, usually based on polymers or viscoelastic surfactants, which serve to control the viscosity of the fluids. Typical viscoelastic surfactants are N-erucyl-N,N-bis(2-hydroxyethyl)-N-methyl ammonium chloride and potassium oleate, solutions of which form gels when mixed with inorganic salts such as potassium chloride and/or with organic salts such as sodium salicylate.

Conventional surfactants, specifically those which tend to form spherical micelles, are generally not capable of forming a viscoelastic composition, particularly an aqueous viscoelastic composition, and are thus not suitable for use in a hydraulic fracturing application. However, certain surfactants, specifically those which tend to form long rod-like or worm-like micelle structures, e.g. viscoelastic surfactants, are capable of forming an aqueous viscoelastic composition. At a relatively low total concentration of a viscoelastic surfactant, typically in the range 1 to 10 wt %, these long rod-like or worm-like micelle structures overlap, forming an entangled network which is viscoelastic. Typically, these large micelle structures are readily destroyed by their interaction with formation fluids such as hydrocarbon fluids. When the micellar structures are broken by their interaction with the hydrocarbon fluid, a solution with low viscosity is formed. If a viscoelastic surfactant based fracturing fluid interacts with produced hydrocarbon fluids, a dramatic change in micellar structure (from rod-like or worm-like to spherical micelles) for instance causes a dramatic change in the rheological properties of the fracturing fluid (from a viscoelastic composition to an inviscid solution). It is this "responsive" fluid which facilitates easy removal and clean up of the fluid from the propped fracture so as to maximise hydrocarbon production.

The application of viscoelastic surfactants in both non-foamed and foamed fluids used for fracturing subterranean formations has been described in several patents, e.g. EP-A-0835983, U.S. Pat. Nos. 5,258,137, 5,551,516, 5,964,295 and 5,979,557.

The use of viscoelastic surfactants for water shut off treatments and for selective acidizing is discussed in GB-A-2332224 and Chang F. F., Love T., Affeld C. J., Blevins J. B., Thomas R. L. and Fu D. K., "Case study of a novel acid diversion technique in carbonate reservoirs", Society of Petroleum Engineers, 56529, (1999).

The use of amide sulphonates in oilfield applications is also known. For example, N-acyl N-methyl taurates have been used as foaming agents in foam drilling and workover applications (U.S. Pat. No. 3,995,705) and as scale inhibitors in acidising formulations (U.S. Pat. Nos. 3,924,685, 3,921,718 and U.S. Pat. No. 3,921,716). Of these, for example, U.S. Pat. No. 3,924,685 describes a method of increasing and sustaining production of fluids from a subterranean fluid-bearing formation by injecting an aqueous solution containing a water-soluble substituted taurine, such as N-oleoyl N-methyl taurate, sodium N-palmitoyl N-methyl taurate or sodium N-acyl N-methyl taurate. This patent does not, however, (i) demonstrate that such water-soluble substituted taurine compounds can form viscoelastic gels or (ii) describe any methods to cause an increase in the viscosity of the fluid. Thus, although amide sulphonates have found use as surfactants in a variety of oilfield applications, they have not been used in the preparation of viscoelastic surfactant gels.

SUMMARY OF THE INVENTION

Broadly, the present invention provides a wellbore fluid which is an aqueous viscoelastic composition comprising a cleavable surfactant.

The term "cleavable surfactant" as used herein means a surfactant having at least one chemical bond within the molecule which may be broken at a controlled rate under appropriate conditions of temperature and/or pH, to produce smaller fragments of the molecule. A cleavable surfactant may also be referred to as a "degradable", "temporary", or "self-destructive" surfactant.

Following cleavage of at least one chemical bond within a cleavable surfactant, the rheological properties e.g. viscosity of an aqueous viscoelastic composition are usually altered. The cleavage or breakdown products of the cleavable surfactant, are typically either more soluble in oil, or more soluble in water, than the original surfactant molecule. Therefore, the breakdown products have no interfacial properties and are non-surface active in comparison with the surfactant molecule. Thus, cleavage of the cleavable surfactants comprising an aqueous viscoelastic composition in accordance with the present invention, eliminates viscosifying, viscoelastic and surfactant properties of said composition, thereby reducing the potential of a surfactant to form emulsions with a fluid such as for example, a hydrocarbon-containing formation fluid. Advantageously, therefore, aqueous viscoelastic compositions according to the present invention are suitable for application in a wellbore service fluid, particularly a hydraulic fracturing fluid for fracturing subterranean formations, or a well clean-out fluid, where the compositions of the present invention obviate the difficulties encountered with the non-cleavable viscoelastic surfactants of the prior art. Conveniently, the elimination of the viscosifying, viscoelastic and surfactant properties of an aqueous viscoelastic composition as outlined above, facilitates the easy removal and clean-up of a fluid from the propped fracture and additionally reduces the potential of a surfactant to form unwanted, stable emulsions. Moreover, generally, as a chemical bond of the cleavable surfactant can be broken under appropriate conditions, the rate of conversion from a viscoelastic composition to a low viscosity solution can be controlled, and therefore the efficiency with which the wellbore service fluid may be removed by the formation fluid is typically improved.

The aqueous viscoelastic compositions of the present invention may suitably be in the form of a solution, or gel, and the like.

Typically, a cleavable surfactant will be added to an aqueous composition e.g. water. Generally, the form of this composition may alter with the addition of optional additives e.g. electrolytes, where the term "electrolyte" as used herein means a compound which undergoes partial or complete dissociation into ions in solution. Preferably, a source of electrolytes is added to a composition comprising a cleavable surfactant to increase the viscosity of the composition so that for example, the composition forms a gel.

Thus the present invention includes an aqueous viscoelastic composition comprising a cleavable surfactant and an electrolyte.

Therefore, in a preferred embodiment herein, generally, the aqueous viscoelastic composition comprises a sufficient quantity of electrolyte, being at least one inorganic or organic water soluble salt, or mixtures thereof.

Typical inorganic water soluble salts suitable for use herein include alkali metal salts and the like such as potassium and ammonium salts e.g. potassium chloride, tetramethyl ammonium chloride and ammonium chloride; alkaline earth metal halides such as calcium chloride, calcium bromide and magnesium chloride; transition metal salts such as zinc halide salts, aluminium salts, zirconium salts and the like; and salts which dissolve in aqueous solution to release divalent anions such as for example sulfate or carbonate anions etc.

Suitable organic water soluble salts for use herein typically involve a sodium or potassium salt of an organic anion. The anion may be an aromatic organic anion such as a salicylate, naphthalene sulfonate, p- and m-chlorobenzoates, 3,5 and 3,4 and 2,4-dichlorobenzoates, t-butyl and ethyl phenate, 2,6 and 2,5-dichlorophenates, 2,4,5-trichlorophenate, 2,3,5,6-tetra-chlorophenate, p-methyl phenate, m-chlorophenate, 3,5,6-trichloropicolinate, 4-amino-3,5,6-trichloropicolinate, 2,4-dichlorophenoxyacetate, toluene sulfonate, a,b-napthols, pp-'bisphenol A or cocoamidopropyl dimethyl amine oxide.

Preferably, the electrolyte is an inorganic water soluble salt, preferably an alkali metal salt and more preferably a potassium salt.

The optimum choice of electrolyte is determined by the structure and properties of the cleavable surfactant and is normally chosen such that the strength and temperature tolerance of the aqueous viscoelastic composition, typically a gel, is maximised. Additionally, an electrolyte is chosen which is compatible with the counterion of the cleavable surfactant so that undesirable precipitates are not formed. The concentration at which an electrolyte is employed is typically dependent upon the nature of the electrolyte and the type of cleavable surfactant.

Whether a composition according to the present invention can be described as viscoelastic depends on a number of factors which include for example, the concentration of the cleavable surfactant, the nature of the cleavable surfactant, and the type and concentration of the electrolyte. A determination of whether any particular aqueous composition is viscoelastic will be readily determined by a person skilled in the art employing a suitable test for viscoelasticity.

For example, the viscoelasticity of an aqueous composition may be measured by carrying out dynamic oscillatory rheological measurements on the composition as generally described in Barnes H. A. et al., *An Introduction to Rheology*, Elsevier, Amsterdam (1997). In a typical dynamic oscillatory experiment, the composition is sheared sinusoidally according to the following equation (1):

$$\gamma(t) = \gamma_{(max)} \sin \omega t \qquad (1)$$

Where $\gamma(t)$ is the strain, $\gamma(max)$ is the maximum strain, t is time and $\omega$ is the angular frequency. The shear stress, $\sigma$, is given by:

$$\sigma(t) = \sigma_{(max)} \sin(\omega t + \delta) \qquad (2)$$

where $\delta$ is the phase angle.

The relative inputs given by the elastic component (G') and viscous component (G") are resolved as follows. Expanding the sine function in equation (2) gives equations (3) and (4) as follows:

$$\sigma(t) = \sigma_{(max)}[\sin \omega t \cos \delta + \cos \omega t \sin \delta] \qquad (3)$$

$$\sigma(t) = \gamma_{(max)}[G' \sin \omega t + G'' \cos \omega t] \qquad (4)$$

where $G' \equiv (\sigma_{(max)}/\gamma_{(max)}) \cos \delta$ and $G'' \equiv (\sigma_{(max)}/\gamma_{(max)}) \sin \delta$.

Equation (4) therefore defines two dynamic moduli: G', the storage modulus or elastic component and G", the loss modulus or viscous component of a composition having viscoelastic properties.

Preferably, the aqueous viscoelastic composition of the present invention is an aqueous viscoelastic gel, where the term "viscoelastic gel" as used herein means a composition in which the elastic component (G') is at least as important as the viscous component (G"). In other words the elastic (or storage) modulus G' of the fluid is equal to or greater than the loss modulus G". These can be measured using an oscillatory shear rheometer (such as a Bohlin CVO 50) at a frequency of 1 Hz. The measurement of these moduli is described in *An Introduction to Rheology*, by H. A. Barnes, J. F. Hutton, and K. Walters, Elsevier, Amsterdam (1997). In the evolution from a predominantly viscous liquid to a viscoelastic gel, the gel point can be defined by the time when the contribution from the elastic and viscous components becomes equal, i.e. G'=G"; at and beyond this point in time, G'≥G" and the phase angle, δ is ≥45°.

Cleavable surfactants useful herein are capable of forming rod-shaped or worm-like micelles as opposed to spherical micelles or sheet-like structures, therefore they may be referred to as cleavable, viscoelastic surfactants. The formation of these rod-shaped micellar structures typically increases the viscosity of an aqueous composition comprising the surfactants which are generally present in the composition at a concentration in the range 1% to 10% by weight, such that viscoelastic properties are imparted to the composition. The ability of a surfactant to form worm-like micelles and to impart viscoelastic properties to an aqueous composition depends on a number of factors, as has been described hereinabove.

Further, cleavable surfactants useful in the compositions of the present invention generally have the ability to form rod-shaped micelle structures over a broad range of concentrations. Generally, an aqueous viscoelastic composition according to the present invention comprises from about 1% to about 10% by weight of the composition of a cleavable surfactant.

Cleavable surfactants useful herein typically comprise a hydrophobic group linked to a hydrophilic group via a breakable chemical bond, referred to hereinafter for brevity and simplicity as a "linkage". The linkage is such that it may be cleaved under certain conditions e.g. temperature and pH, at a desired and appropriate time, to produce at least one oil soluble and at least one water soluble product.

In general terms, the hydrophobic group is usually a linear or branched hydrocarbon chain which is either fully saturated or partially unsaturated.

Typically, the linkage is suitably an acetal, amide, ether or ester group, although other groups having weak chemical bonds, which can be broken for example by hydrolysis at a controlled rate, under acid or alkaline conditions may be possible. Preferably, the linkage is an acetal, amide or ester group.

Cleavable surfactants, as such, are known for use for example in detergent and personal care products such as fabric softeners and hair conditioners as described in *Novel Surfactants*, edited by K. Holmberg, Marcel Dekker Inc., New York, (1998), ISBN:0-8247-0203-4, see Chapters 4 and 11 pp 115-138 and 333-358 respectively. However, there is no discussion of such surfactants being used to formulate viscoelastic compositions, particularly viscoelastic gels, as the formation of these types of structures would generally be undesirable in such product types.

More specifically, a first aspect of the present invention provides a wellbore fluid comprising an anionic viscoelastic surfactant of formula I:

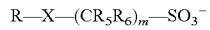

in which:

R is a saturated or unsaturated, linear or branched aliphatic hydrocarbon chain comprising from 6 to 22 carbon atoms, including mixtures thereof and/or optionally incorporating an aryl group;

X is $-(C=O)N(R_7)-$, $-N(R_7)(C=O)-$, $-N(R_7)-$, $-(C=O)O-$, $-O(C=O)-$ or $-O(CH_2CH_2O)_p-$ where p is 0 or an integer of from 1 to 5;

$R_5$ and $R_6$ are each independently hydrogen or a linear or branched saturated aliphatic hydrocarbon chain of at least 1 carbon atom or a linear or branched saturated aliphatic hydrocarbon chain of at least 1 carbon atom with one or more of the hydrogen atoms replaced by a hydroxyl group; or when X is $-N(R_7)(C=O)-$ or $-O(C=O)-$, the group $(CR_5R_6)$ may include a $COO^-$ group;

$R_7$ may be hydrogen, a linear saturated aliphatic hydrocarbon chain of at least 1 carbon atom, a branched saturated aliphatic hydrocarbon chain of at least 2 carbon atoms, a linear saturated aliphatic hydrocarbon chain of at least 1 carbon atom or a branched saturated aliphatic hydrocarbon chain of at least 2 carbon atoms with one or more of the hydrogen atoms replaced by a hydroxyl group, or a cyclic hydrocarbon group; and m is an integer of from 1 to 4;

in the form of a monomeric unit, dimer or oligomer.

The term "aliphatic", when used herein, pertains to compounds and/or groups which are linear or branched, but not cyclic (also known as "acyclic" or "open-chain" groups).

By an "oligomeric" or "oligomer" surfactant we mean that the structure of the surfactant is based on from two to eight (and preferably two to five) linked surfactant monomer units. The monomer units are linked in the oligomer either head group-to-head group or tail group-to-tail group.

In a further aspect, the present invention also provides the use of a viscoelastic surfactant of formula I as hereinabove defined, as a wellbore treatment fluid.

In a yet further aspect, the present invention provides a method for the preparation of a viscoelastic surfactant of formula I as hereinabove defined.

The present inventors have now surprisingly discovered that several previously unknown important benefits are associated with the use of sulphonate as the charged hydrophilic head group in a viscoelastic surfactant specifically having formula I as herein above defined. These important benefits include:

1. Sulphonate surfactants are soluble in and can form viscoelastic gels in aqueous solutions adjusted to or buffered at a wide range of pH conditions. For example, viscoelastic gels based on sulphonate surfactants can be formulated under pH conditions ranging from strongly acidic through neutral to strongly alkaline conditions. This leads to their potential application in matrix acidising and associated diversion systems, acid fracturing and neutral/alkaline fracturing fluids. Further, we note that the properties of viscoelastic gels based on sulphonate surfactants may depend on pH which leads to the potential for designing gels which subsequently de-gel on changing the prevailing pH condition. This effect introduces an additional feature which may be used in delayed gelation systems or in systems designed to de-gel for improved clean-up. It is noted here that acidic, neutral or alkaline gels based on viscoelastic sulphonate surfactants are easily broken down by interaction with hydrocarbons.

2. Many sulphonate surfactants are well known to be good foamers [Porter, M. R., "Handbook of Surfactants", 2nd Edition, Blackie Academic & Professional, Chapman & Hall, 1994) and they have found particular application in forming stable foams with $CO_2$ as the internal gas or supercritical fluid phase [Heller, J. P. Chapter 5 in "Foams: Fundamentals and Applications in the Petroleum Industry" edited by Schramm, L L. Am Chem Soc Advances in Chemistry Series, 242, 1994 and Borchardt et al., Society Petroleum Engineers (SPE) paper 14394 presented at the 60th Annual Technical Conference, Sep. 22-25, 1985]. Again, this is related to the compatibility of sulphonate surfactants with acid conditions, in this case generated when the external aqueous phase of the foam is equilibrated with a significant partial pressure of $CO_2$ [Chambers, Chapter 9 in "Foams: Fundamentals and Applications in the Petroleum Industry" edited by Schramm, L L. Am Chem Soc Advances in Chemistry Series, 242, 1994]. As discussed in the next section, amide sulphonate surfactants and, in particular, di-substituted taurates have already found oilfield application in foam drilling [U.S. Pat. No. 3,995,705] and in acidising fluids with improved scale inhibition properties [U.S. Pat. Nos. 3,924,685, 3,921,718 and 3,921,716]. The potential for viscoelastic surfactants which are both chemically compatible with $CO_2$ and which can produce stable $CO_2$ foams provides an opportunity for highly cost-effective foamed fracturing fluids based on $CO_2$ co-injected with an aqueous viscoelastic surfactant gel phase. Such technology has important application in certain key markets.

3. It is well known that carboxylate surfactants are more sensitive to the presence of polyvalent cations than the corresponding phosphates, sulphates or sulphonates [Porter, M. R., "Handbook of Surfactants", 2nd Edition, Blackie Academic & Professional, Chapman & Hall, 1994]. Thus, sulphonate VES are compatible with a higher concentration of divalent cations (e.g. $Ca^{++}$, $Mg^{++}$) present in the mixwater used to prepare the fluid or in backflowing formation brine as compared to carboxylate VES. Therefore, when using fracturing fluids based on sulphonate VES there is a lesser need to add divalent cation chelating agents (e.g. EDTA) to the formulation; this has important operational advantages. Furthermore, when the sulphonate VES is an amide sulphonate such as N-oleyl or N-tallowyl N-methyl taurate, the VES component also inhibits scale formation (as per the discussion given in U.S. Pat. Nos. 3,924,685, 3,921,718 and 3,921,716).

4. In any application of a viscoelastic surfactant as a wellbore service fluid (e.g. as a fracturing fluid) it is an important operational advantage that the VES can be delivered to the flowstream in the form of an easily pumpable liquid containing a high concentration of active viscoelastic surfactant. In the case of sulphonate VES, this can be achieved by liquifying the active component in its neutral or salt form. For example, the VES N-oleyl N-methyl taurate can be delivered via a liquid concentrate containing a high concentration of its sodium or potassium salt. Depending on the application, this neutral concentrate can be metered into an acidic brine stream (acid fracturing) or neutral/alkaline brine stream (neutral/alkaline fracturing) in order to form the viscoelastic gel as required. Furthermore, a neutral viscoelastic gel can be delivered without the need for the addition of any acid or alkali.

Examples of suitable anionic cleavable surfactants useful in the aqueous viscoelastic compositions of the present invention include surfactants shown by the following formulae:

Formula (IA)(i)

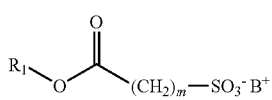

Formula (IA)(ii)

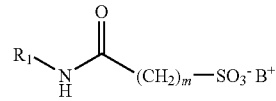

Formula (IA)(iii)

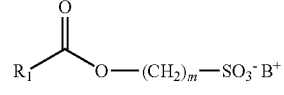

Formula (IA)(iv)

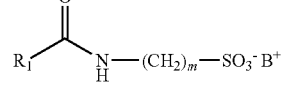

where $R_1$ is a saturated or unsaturated, linear or branched aliphatic chain of at least 18 carbon atoms; m is at least one, preferably m is at least two, and when m is ≥3, m may be a straight or branched alkyl chain; $B^+$ is an ionic counterion where typically, for example, $B^+$ is hydrogen or a monovalent cation such as an alkali metal ion and the like e.g. potassium or sodium etc.

$R_1$ may be an aliphatic chain of at least 20 carbon atoms and more preferably at least 22 carbon atoms. Generally, there are no constraints on the maximum chain length of $R_1$, provided that the cleavable surfactant as an entity is water-soluble in an aqueous composition.

The cleaved products of a cleavable surfactant generally comprise at least one water-soluble and one water-insoluble product.

When the linkage of a cleavable surfactant is an amide or ester group, the carbonyl carbon atom may be positioned closer to the hydrophilic group e.g. an O(CO) or HN(CO) group, thereby forming 'reverse' esters or amides. These types of cleavable surfactants containing reverse esters or amides (typically represented by formulae 2(i) and 2(ii) above) may be cleaved to give (i) a water-insoluble alcohol or amine product, e.g. a long chain alcohol $R_1$—OH, or long chain amine, $R_1$—$NH_2$ and (ii) a water-soluble acid product e.g. $HOOC(CH_2)_mSO_3^-$.

Alternatively, when the carbonyl carbon atom of an ester or amide linkage is positioned away from the hydrophilic group e.g. a (CO)O or (CO)NH group, such surfactants (typically represented by formulae 2(iii) and 2(iv) above) may be cleaved to give (i) an acid product and (ii) a water-soluble alcohol or amine type product e.g. E-$(CH_2)_m$—F where E is OH (ester version) or $NH_2$ (amide version) and F is $SO_3^-$.

Cleavable surfactants useful in the aqueous viscoelastic compositions described herein may be prepared according to a number of synthetic routes.

In one approach, a cleavable surfactant may be synthesised by coupling either a long chain alcohol or amine with an acid halide having a hydrophilic group, specifically a sulphonate group, attached at the opposite end of the hydrocarbon chain e.g. —$(CH_2)_m$— as described in March J. *Advanced Organic Chemistry*, 3rd Edition, John Wiley & Sons, New York (1985); Kaiser et al., *Journal of Organic Chemistry*, 1970, 35, 1198; Kivinen, in Patai, *The Chemistry of Acyl Halides*, pp 177-230, Interscience, New York (1972); Satchell, Q. *Rev. Chem. Soc.* 1963, 17, 160-203; Butler et al. *J. Chem. Soc.* 1961, p 4362; Fersht et al. *J. Am. Chem. Soc.* 1970, 92, 5432; and Challis and Challis, in Zabicky, *The Chemistry of Amides*, Interscience, New York (1970); all of which are incorporated herein by reference. A typical and representative example of such reaction is:

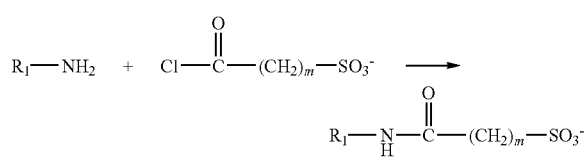

Alternatively, a cleavable surfactant can be synthesised by coupling either a carboxylic acid or carboxylic acid halide with an alcohol or amine having a hydrophilic $SO_3^-$ group attached at the opposite end of the hydrocarbon chain.

Typically, the rate at which the linkage of the cleavable surfactant can be broken is dependent upon the pH of the aqueous viscoelastic composition and the temperature. Under the appropriate conditions therefore, as the cleavable surfactants are degraded, the aqueous viscoelastic composition loses its viscoelasticity, such that the contribution from the elastic modulus (G') in the composition becomes less than that of the viscous modulus (G"). The resulting composition is therefore a low viscosity fluid exhibiting near-Newtonian or Newtonian behaviour. Typically therefore, the rate of conversion of an aqueous viscoelastic composition to a low viscosity fluid can be controlled and is generally dependent upon the decomposition rate of the cleavable surfactants.

Generally, for any of the above-mentioned cleavable surfactants, the higher the temperature, the faster the rate of cleavage of the cleavable surfactant. Specifically, when the linkage of a cleavable surfactant is an ester group, the decomposition rate attains a maximum under high pH (alkaline) conditions. Conversely, for cleavable surfactants comprising as the linkage an amide group, the decomposition rate is at a maximum under low pH (acidic) conditions. Low pH, that is to say acidic, conditions can also be used to cleave cleavable surfactants when the linkage is an acetal.

In general, the oil-soluble and water-soluble products produced from a cleavable surfactant, are not themselves capable of producing a viscoelastic composition. For cleavable surfactants comprising as the degradable linkage, an ester or amide group, two main types have been described above: those which degrade to give a long chain alcohol or amine, and those which degrade to give a long chain carboxylic acid. Typically, long chain alcohols are not known to form viscoelastic compositions. Similarly, long chain amines do not typically form viscoelastic compositions. However, long chain carboxylic acids may form viscoelastic compositions when in the deprotonated form; therefore, in designing a composition using the cleavable surfactants shown for example, in formulae 2(iii) and 2(iv) above, it is generally important to ensure that acidic conditions are maintained after cleavage of the surfactant.

The aqueous viscoelastic compositions of the present invention may optionally comprise additional viscoelastic surfactants as described for example in U.S. Pat. Nos. 5,258,137; 5,551,516; 5,964,295 and 5,979,557; all of which are hereby incorporated by reference.

The aqueous viscoelastic compositions according to the present invention are preferably a wellbore service fluid or treatment fluid, more preferably a hydraulic fracturing fluid, or a well clean-out fluid, and even more preferably an aqueous fracturing fluid.

To prepare a wellbore service fluid, particularly a hydraulic fracturing fluid, or a well clean-out fluid, more particularly an aqueous fracturing fluid, the cleavable surfactant is generally added to an aqueous solution in which has been dissolved a quantity of electrolyte, typically at least one inorganic or organic water soluble salt. If fluid density becomes an important consideration, heavier electrolytes may be employed. Standard mixing procedures known in the art can be employed since heating of the solution and special agitation conditions are normally not necessary. Of course, if used under conditions of extreme cold such as found in Alaska or Canada, normal heating procedures should be employed.

Sometimes it is preferable to dissolve the cleavable surfactant into a lower molecular weight alcohol prior to mixing it with the aqueous solution. The lower molecular weight alcohol or diol, for instance isopropanol or propylene glycol, may function to liquify the surfactant concentrate and therefore aid the solubilisation of the cleavable surfactant on mixing with the aqueous solution. Other similar agents may also be employed, notably lower molecular weight amines. Further, a defoaming agent such as a polyglycol may be employed to prevent undesirable foaming during the preparation of the fracturing fluid if a foam is not desirable under the conditions of the treatment. If a foamed fluid is desired, a gas such as air, nitrogen, carbon dioxide or the like may be employed.

In addition to the electrolytes and cleavable surfactants described herein, the wellbore service fluid may contain other conventional constituents which perform specific desired functions, e.g., corrosion inhibitors, fluid-loss additives, and others as described previously herein, and the like. A proppant can then be suspended in the wellbore service fluid.

Generally, in use, the micellar structures formed by the cleavable surfactants and the interactions between such micellar structures of the wellbore service fluid are readily altered by shear rate conditions, the presence of hydrocarbons, or by increased temperature. All of these features may be found in the hydrocarbon portion of the reservoir. Typically, the cleavable surfactant worm-like micelle structures are destroyed as they interact with the fluids produced from the hydrocarbon-bearing formation. At this stage, the worm-like micellar structures are no longer required to impart the high viscosity required to transport particles such as the proppant into the fracture. Additionally, after a period of time the cleavable surfactant molecules conveniently decompose to form breakdown products which are either soluble in water or soluble in oil. The oil-soluble products may be extracted with the produced hydrocarbon fluids and the water-soluble products with the produced water.

Therefore, according to an even further aspect of the present invention, there is provided a method of fracturing a subterranean formation, comprising the steps of:

(A) providing a wellbore service fluid comprising a cleavable surfactant in accordance with this invention, and (B) pumping the fluid through a wellbore and into a subterranean formation at a pressure sufficient to fracture the formation.

DETAILED DESCRIPTION

Figure 1:
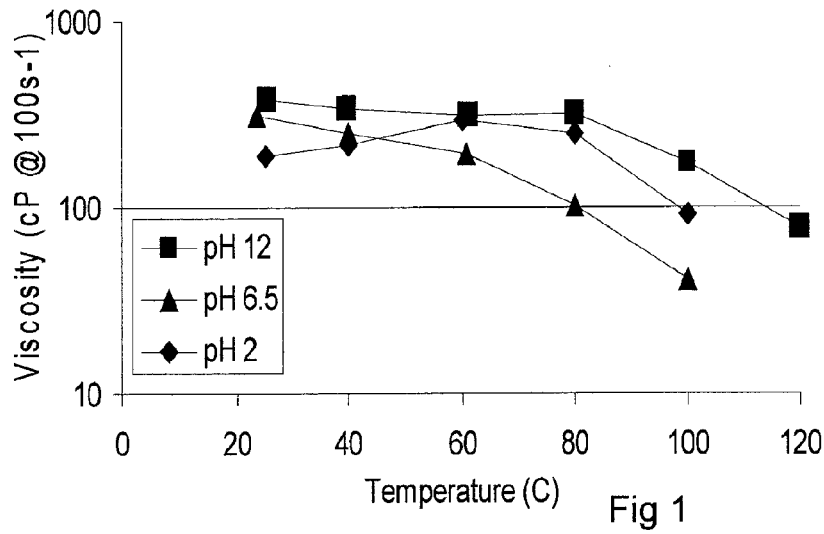
FIG. 1: demonstrates the ability of the surfactant N-oleyl N-methyl taurate to form viscous fluids in a wide range of pH conditions and the maintenance of viscosity at temperatures from room temperature up to the range 180-240° F. (82-115° C.).
Figure 2:
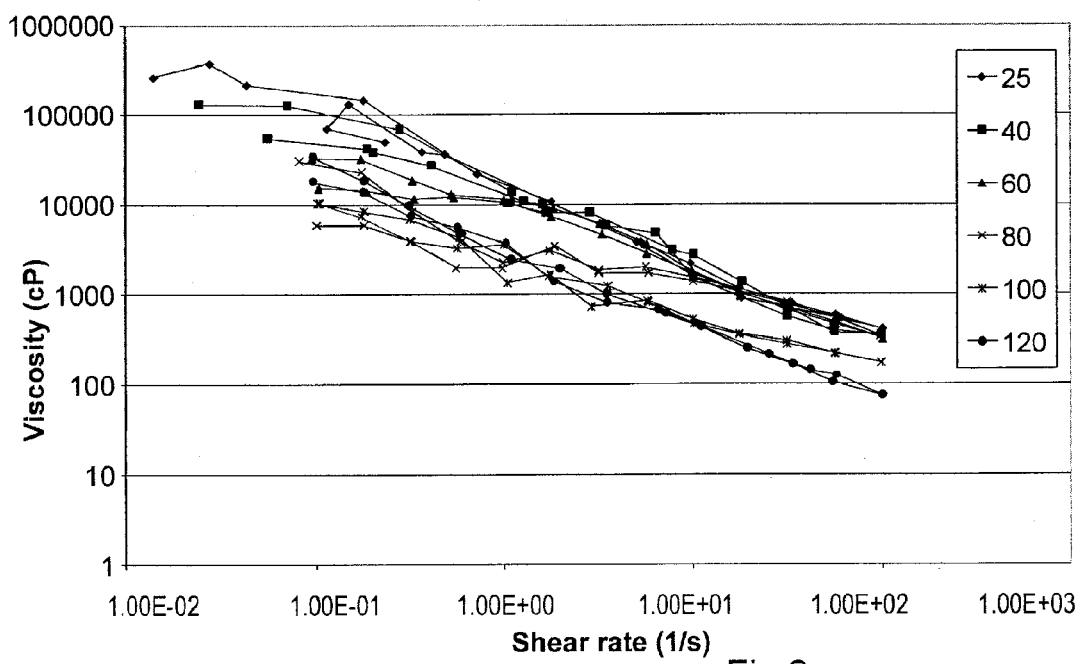
FIG. 2: shows the full rheograms corresponding to the data illustrated in FIG. 1 for the fluid at pH 12. The fluids are viscoelastic gels and viscoelasticity is assessed by measurement of dynamic (oscillatory) rheology.

As already stated above, the present invention provides, in one aspect, a wellbore fluid containing an anionic viscoelastic surfactant of formula I:

in which:
R is a saturated or unsaturated, linear or branched aliphatic hydrocarbon chain comprising from 6 to 22 carbon atoms, including mixtures thereof and/or optionally incorporating an aryl group;
X is —(C=O)N($R_7$)—, —N($R_7$)(C=O)—, —N($R_7$)—, —(C=O)O—, —O(C=O)— or —O($CH_2CH_2O$)$_p$— where p is 0 or an integer of from 1 to 5;

$R_5$ and $R_6$ are the same or different and are each independently hydrogen or a linear or branched saturated aliphatic hydrocarbon chain of at least 1 carbon atom or a linear or branched saturated aliphatic hydrocarbon chain of at least 1 carbon atom with one or more of the hydrogen atoms replaced by a hydroxyl group; or
when X is —N($R_7$)(C=O)— or —O(C=O)—, the group ($CR_5R_6$) may include a $COO^-$ group;
$R_7$ may be hydrogen, a linear saturated aliphatic hydrocarbon chain of at least 1 carbon atom, a branched saturated aliphatic hydrocarbon chain of at least 2 carbon atoms, a linear saturated aliphatic hydrocarbon chain of at least 1 carbon atom or a branched saturated aliphatic hydrocarbon chain of at least 2 carbon atoms with one or more of the hydrogen atoms replaced by a hydroxyl group, or a cyclic hydrocarbon group; and m is an integer of from 1 to 4;
in the form of monomeric unit, a dimer or oligomer.

By an "oligomeric" or "oligomer" surfactant we mean that the structure of the surfactant is based on from two to eight (and preferably two to five) linked surfactant monomer units. The monomer units are linked in the oligomer either head group-to-head group or tail group-to-tail group. When they are linked head group-to-head group, the oligomer has distinct tail groups corresponding to the tail groups of the monomer units and a super-head group formed from the plural head groups of the monomer units. When they are linked tail group-to-tail group, the oligomer has distinct head groups corresponding to the head groups of the monomer units and a super-tail group formed from the plural tail groups of the monomer units.

Although the oligomer is defined above in relation to a chemically-corresponding monomer unit, in practice the oligomer surfactant may not necessarily be synthesised from that monomer. For example, a synthesis route may be adopted in which monomer units are first oligomerised and the head groups are then changed to those of the desired oligomer surfactant. That is the head groups of the monomer units used in practice to form the oligomer may be different from the head groups of the monomer units to which the oligomer chemically corresponds. In another example, if the tail groups of the monomers actually used to form the oligomer are unsaturated, the oligomerisation process may involve the partial or total hydrogenation of those groups, particularly if the tail groups are linked in the oligomer.

Furthermore the tail groups of the monomer units actually used to form the oligomer may be aliphatic, but if the monomer units are linked in the oligomer tail group-to-tail group, the links formed between the tail groups in the super-tail group may be aliphatic, alicyclic or aromatic.

In the compound of formula I above, R is a saturated or unsaturated, linear or branched aliphatic hydrocarbon chain comprising from 6 to 22 carbon atoms, including mixtures thereof and/or optionally incorporating an aryl group.

R can be a mixture of saturated and unsaturated hydrocarbon chains obtained from fatty acid(s) derived from a number of natural oils and fats including, for example, coconut oil, tallow oil, tall oil, soya bean or rapeseed oil.

Preferably R has a composition and/or degree of unsaturation which is sufficient to render the surfactant soluble in water at the typical surface temperatures prevailing in an oilfield wellsite environment. Thus, as defined by the iodine value (IV—which is a measure of the unsaturation of the fatty acids and is expressed in terms of the number of centigrams of iodine absorbed per gram of sample) of the fatty acid or fatty acid mixture, the range of unsaturation should be within the IV range of 1-200 and preferably within the IV range of 40-110.

Preferably, R is a fully or partially saturated, linear or branched hydrocarbon chain of at least 15 carbon atoms and preferably of from 16 to 22 carbon atoms. More preferably, R is derived from fatty acids such as palmitic acid, erucic acid, oleic acid, coconut oil acid, tallow acid, tall oil acid, soya oil acid or rapeseed oil acid. The physical appearance, iodine value, acid value and composition of oleic acid, tallow acid and tall oil acid are compared to the same properties of stearic acid in the table given below:

| Typical Fatty Acid Compositions | | | | |
|---|---|---|---|---|
| | Fatty Acid | | | |
| | Stearic Acid | Tallow Acid | Oleic Acid | Tall Oil Fatty Acid |
| Physical appearance (25° C.) | Solid powder | High viscosity slurry | Low viscosity oil | Low viscosity oil |
| Iodine Value | 1 max | 50-55 | 105-125 | 131 |
| Acid Value | 202-209 | 203 | 194-210 | 194 |
| Typical compositions | | | | |
| C15 & lower | | 3 | 3 | 5 |
| C16 = 1 | | 31 | 25 | |
| C18 | 65 | 17 | 2 | 5 |
| C18 = 1 | | 50 | 59 | 51 |
| C18 = 2 | | 5 | 23 | 35 |
| C18 = 3 | | | 11 | 9 |

Notes: (i) The iodine value is a measure of the unsaturation of the fatty acid mixture and is expressed in terms of the number of centigrams of iodine absorbed per gram of sample, (ii) The acid value is a measure of the amount of alkali required to neutralise the fatty acid expressed in terms of the number of milligrams of potassium hydroxide required to neutralise 1 gram of the fatty acid, (iii) C18=1, C18=2 and C18=3 refer to a partially unsaturated hydrocarbon chain composed of 18 carbons atoms in which there is one, two or three double bonds, respectively, (iv) the "Typical compositions" data are quoted as weight percentages.

In the compound of formula I, $R_5$ and $R_6$ are the same or different and are each independently hydrogen, a linear saturated aliphatic hydrocarbon chain of at least 1 carbon atom, a branched saturated aliphatic hydrocarbon chain of at least 2 carbon atoms, a linear saturated aliphatic hydrocarbon chain of at least 1 carbon atom or a branched saturated aliphatic hydrocarbon chain of at least 2 carbon atoms with one or more of the hydrogen atoms replaced by a hydroxyl group; or, when X is —N($R_7$)(C═O)— or —O(C═O)—, the group (CR$_5$R$_6$) may include a COO$^-$ group. Preferably, in these compounds, $R_5$ and $R_6$ are the same and are each hydrogen or a linear $C_{1-6}$alkyl or branched $C_{2-6}$alkyl group, more preferably hydrogen or a methyl or ethyl group.

In the compounds of formula I, $R_7$ is hydrogen, a linear saturated aliphatic hydrocarbon chain of at least 1 carbon atom, a branched saturated aliphatic hydrocarbon chain of at least 2 carbon atoms, a linear saturated aliphatic hydrocarbon chain of at least 1 carbon atom or a branched saturated aliphatic hydrocarbon chain of at least 2 carbon atoms with one or more of the hydrogen atoms replaced by a hydroxyl group, or a cyclic hydrocarbon group. It is generally preferred that $R_7$ is hydrogen or a $C_{1-6}$ alkyl group or a $C_{1-6}$ alkyl group substituted with an aryl group. It is more preferred that $R_7$ is hydrogen, methyl, ethyl, propyl, butyl or an aryl substituted $C_{1-6}$alkyl group and most preferred that $R_7$ is hydrogen or methyl.

In the compound of formula I, m is an integer of from 1 to 4, preferably 2 or 3 and most preferably 2.

In one embodiment of composition of the present invention, the anionic viscoelastic surfactant has formula II:

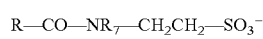
R—CO—NR$_7$—(CR$_5$R$_6$)$_m$SO$_3^-$ i.e. a compound of formula I in which X is —(C═O) NR$_7$—, and in which: R, $R_5$, $R_6$, $R_7$ and m are as defined above; as a monomeric unit, a dimer or an oligomer.

It is then preferred that the anionic viscoelastic surfactant is of formula IIA:

R—CO—NR$_7$—CH$_2$CH$_2$—SO$_3^-$ in which R is as defined above and the group R—CO— is preferably selected from N-cetyl, N-erucyl, N-oleoyl, N-cocoyl, N-tallowyl, N-tallyl, N-soyayl or N-rapeseedyl and most preferably is N-oleoyl; and $R_7$ is as defined above and is preferably hydrogen or a $C_{1-6}$ alkyl group, more preferably hydrogen or methyl; as a monomeric unit, a dimer or an oligomer.

In a further preferred embodiment of composition of the present invention the anionic viscoelastic surfactant has formula III:

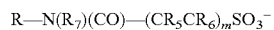
R—N(R$_7$)(CO)—(CR$_5$R$_6$)$_m$SO$_3^-$ i.e. a compound of formula I in which X is —N($R_7$)(C═O)—; and in which R, $R_5$, $R_6$, $R_7$ and m are as defined above; as a monomeric unit, a dimer or an oligomer.

It is preferred that, when of formula III, the anionic viscoelastic surfactant is of formula IIIA:

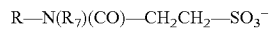
R—N(R$_7$)(CO)—CH$_2$CH$_2$—SO$_3^-$ in which R is as defined above and is preferably derived from fatty acids such as palmitic acid, erucic acid, oleic acid, coconut oil acid, tallow acid, tall oil acid, soya oil acid or rapeseed oil acid; and $R_7$ is as defined above and is preferably hydrogen or a $C_{1-6}$ alkyl group, more preferably hydrogen or methyl;
as a monomeric unit, a dimer or an oligomer.

In another preferred embodiment of composition of the invention, the anionic viscoelastic surfactant has formula IV:

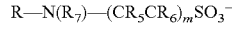
R—N(R$_7$)—(CR$_5$R$_6$)$_m$SO$_3^-$ i.e. a compound of formula I in which X is —N($R_7$)—, and in which R, $R_5$, $R_6$, $R_7$ and m are as defined above; as a monomeric unit, a dimer or an oligomer.

It is preferred that R is derived from fatty acids such as palmitic acid, erucic acid, oleic acid, coconut oil acid, tallow acid, tall oil acid, soya oil acid or rapeseed oil acid; and $R_7$ is as defined above and is preferably hydrogen or a $C_{1-6}$ alkyl group, more preferably hydrogen or methyl; as a monomeric unit, a dimer or an oligomer.

In another preferred embodiment of composition of the invention, the anionic viscoelastic surfactant has formula V:

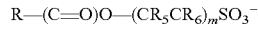
R—(C═O)O—(CR$_5$R$_6$)$_m$SO$_3^-$ i.e. a compound of formula I in which X is —(C═O)O—; in which R, $R_5$, $R_6$ and m are as defined above; as a monomeric unit, a dimer or an oligomer.

It is preferred that, when of formula V, the anionic viscoelastic surfactant is of formula VA:

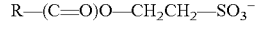
R—(C═O)O—CH$_2$CH$_2$—SO$_3^-$ in which R is as defined above and is preferably derived from fatty acids such as palmitic acid, oleic acid, erucic acid, coconut oil acid, tallow acid, tall oil acid, soya oil acid or rapeseed oil acid.

Ester sulphonate surfactants of formula VA are generally known as "isethionate" surfactants as they may be produced by reacting the acid chloride, R—(C=O)Cl with sodium isethionate, $HOCH_2CH_2SO_3Na$.

Again, compounds of formula V can include the monomeric, dimeric or oligomeric forms.

In another preferred embodiment of composition of the invention, the anionic viscoelastic surfactant has formula VI:

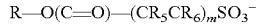

i.e. a compound of formula I in which X is —O(C=O)—; and in which R, R5, R6 and m are as defined above; as a monomeric unit, a dimer or an oligomer.

It is preferred that, when of formula VI, the anionic viscoelastic surfactant is of formula VIA:

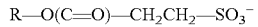

in which R is as defined above and is preferably derived from fatty acids such as palmitic acid, erucic acid, oleic acid, coconut oil acid, tallow acid, tall oil acid, soya oil acid or rapeseed oil acid; as a monomeric unit, a dimer or an oligomer.

In another embodiment of composition of the invention, the anionic viscoelastic surfactant has formula VII:

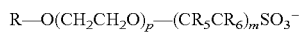

i.e. a compound of formula I in which X is —O($CH_2CH_2O$)$_p$—; and in which R, $R_5$, $R_6$, m and p are as defined above; as a monomeric unit, a dimer or an oligomer.

Most preferred anionic viscoelastic surfactants of the present invention are compounds of formula IIA, for example N-acyl N-methyl taurates, such as N-cetyl N-methyl taurate, N-erucyl N-methyl taurate, N-oleoyl N-methyl taurate, N-cocoyl N-methyl taurate, N-tallowyl N-methyl taurate, N-tallyl N-methyl taurate, N-soyayl N-methyl taurate and N-rapeseedyl N-methyl taurate or N-acyl taurates, such as N-erucyl taurate, N-oleoyl taurate, N-cocoyl taurate, N-tallowyl taurate, N-tallyl taurate, N-soyayl taurate and N-rapeseedyl taurate.

An oligomeric surfactant may be based on linked surfactant monomer units, each monomer unit having a formula as shown in any one of formulae I to VII above. The oligomeric surfactant may be formed as described in, for example, PCT Patent Publication No. WO 02/11874 or using techniques known in the art.

The following scheme illustrates the preparation of dimeric N-oley N-methyl taurate:

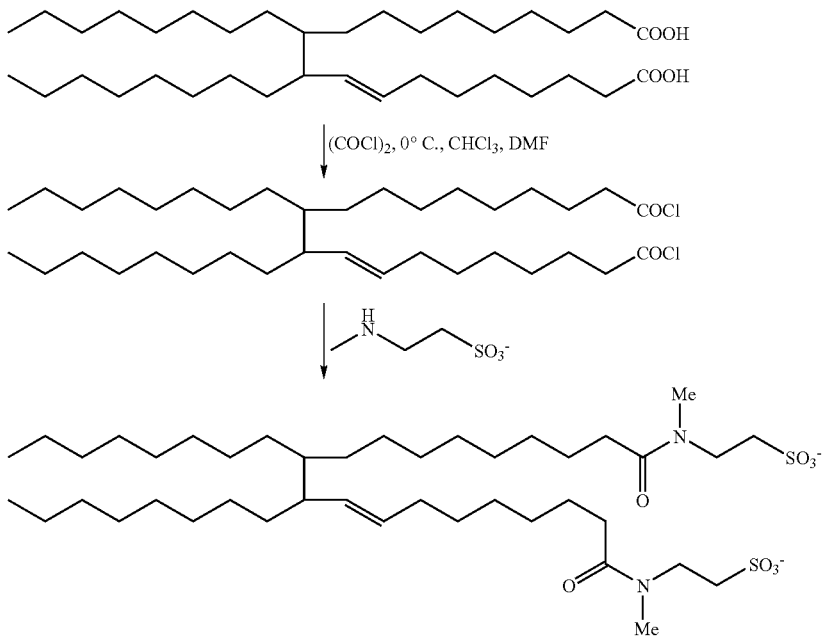

Thus, in respect of the surfactant of formula IIA, above, the acid chloride derivative of an oligomeric fatty acid may be used to prepare oligomeric surfactants of formula IIA, above and having the structure below:

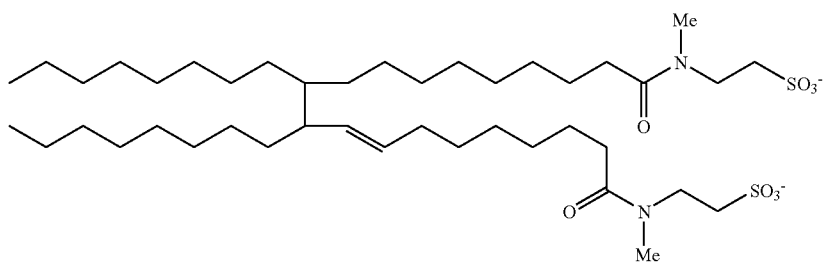

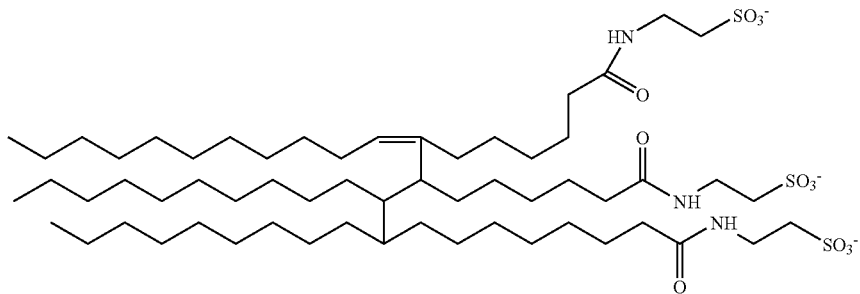

The first structure is di(N-oleyl N-methyl taurate) and the second structure is tri(N-oleyl taurate).

An acid chloride derivative of an fatty acid may be prepared using techniques common in the art, such as those described by Larock in "Comprehensive Organic Transformations: a guide to functional group preparations", $2^{nd}$ Edition, Wiley-VCH, ISBN 0-471-19031-4 (1999).

Typical fatty acids that may be used in the manufacture of oligomeric forms of compounds of formula II or formula III via their corresponding amines include:

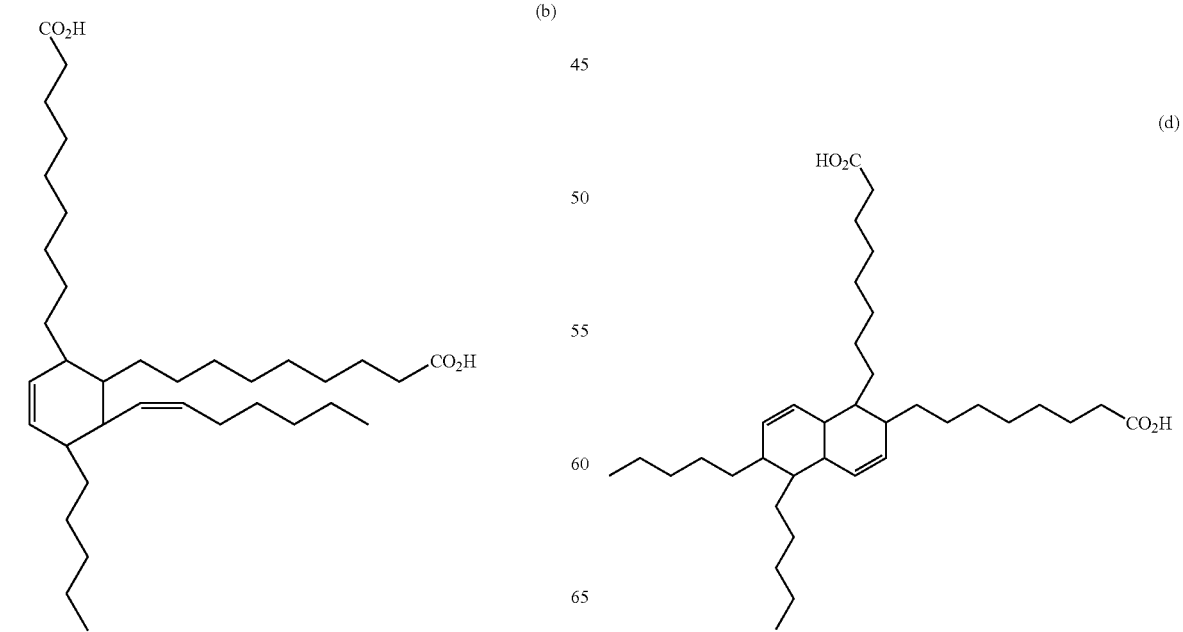
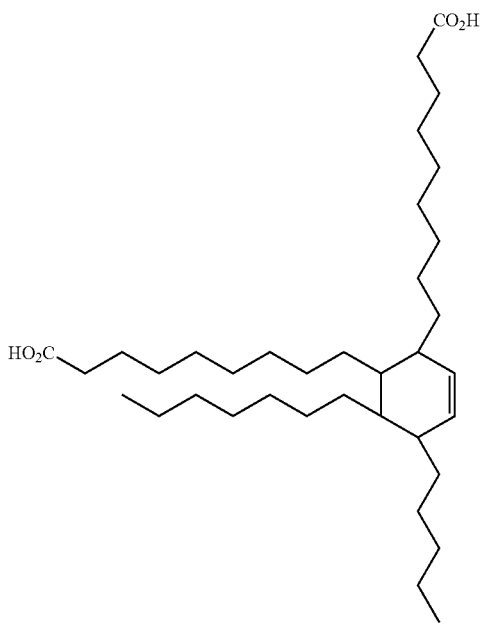

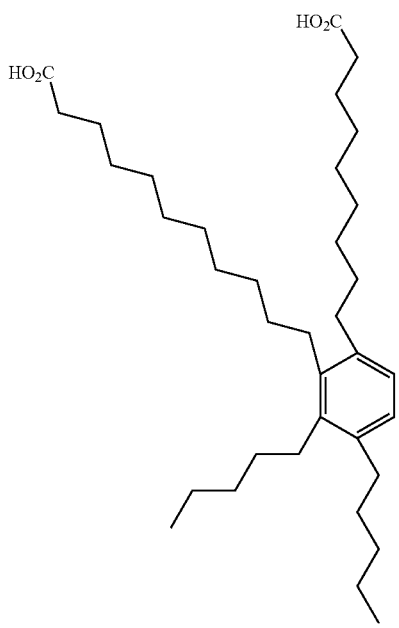

In the above formulae:
(a) is dimerised oleic acid.
(b) is 1,2-dinonanoic-3-hept-1-enyl-4-pentyl-cyclohex-5-ene
(c) is 1,2-dinonanoic-3-heptyl-4-pentyl-cyclohex-5-ene (d) is 1,2-dinonanoic-5,6-dipentyl-bis-cyclohexa-3,7-diene.

(e) is 1,2-dinonanoic-5,6-dipentylbenzene.

Oligomeric amines can be obtained from a large range of oligomeric fatty acids including those shown above. The oligomeric acid can be converted to its equivalent oligomeric amine via the corresponding oligomeric amide, alcohol or nitrile. The oligomeric amine can then be reacted with the sulpho-carboxylic acid as shown in the exemplary synthetic steps for the preparation of compounds of formula III, shown below.

The anionic viscoelastic surfactants of the above formulae may be prepared by methods known in the art.

For the preparation of compounds of formula II, the following synthetic route may be followed:

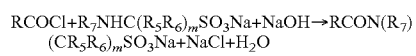

wherein $R_7NHC(R_5R_6)_mSO_3Na$ may be obtained as follows:

in which R, $R_5$, $R_6$, $R_7$ and m are as defined above.

The sodium chloride by-product may optionally be removed, for example by reverse osmosis (JP 04149169).

For the preparation of compounds of formula III, the following synthetic route may be taken as exemplary:

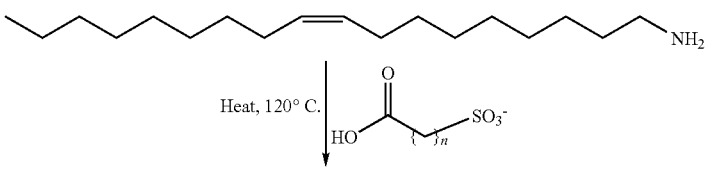

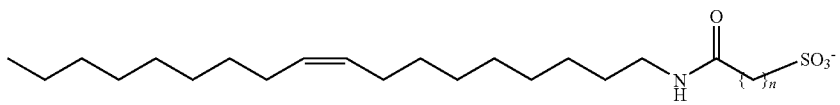

in which n has the same value as m, defined above.

For the preparation of compounds of formula IV, the corresponding amide sulphonate of formula II or III may be reduced. An exemplary synthetic route to the compounds of formula IV is provided below:

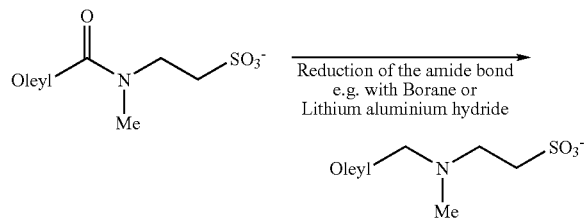

Alternatively, compounds of formula IV may be prepared by reaction of the monomeric or oligomeric amine R—NH$_2$, (wherein R is as previously defined) with compounds of formula OH—CH(R$_5$)—(CR$_5$R$_6$)$_m$—SO$_3^-$, (where R$_5$ and R$_6$ are as defined above). U.S. Pat. No. 2,658,072 describes such a process of producing N-alkyl taurines having the formula RNHC(R')H—CH$_2$SO$_3$X where R is an alkyl radical of from 8 to 18 carbon atoms, R' is either hydrogen or methyl and X is either hydrogen, alkali metal, alkaline earth metal or ammonium. The examples in this reference detail process conditions for reacting N-tetradecylamine, N-octylamine, N-dodecylamine and "cocamine" with sodium isethionate; the patent includes data which show that the N-alkyl taurine products maintain good detergent and foaming properties in waters with hardness up to 300 p.p.m.

For the preparation of a compound of formula V, the following method may be followed:

RCOCl+OH—CH(R$_5$)—(CR$_5$R$_6$)$_m$—SO$_3$Na→RCOO(CR$_5$R$_6$)$_m$SO$_3$Na+HCl in which m, R, R$_5$ and R$_6$ are as previously defined.

For the preparation of a compound of formula VI, the following method may be followed:

and U.S. Pat. Nos. 2,098,203, 2,106,716 and 2,115,192 (all three patents are assigned to the company Rohm and Hass). The reaction is shown below:

RO(CH$_2$CH$_2$O)$_p$H+epichlorohydrin(ClC$_3$H$_5$O)+
Na$_2$SO$_3$→RO(CH$_2$CH$_2$O)$_p$CH$_2$—CH(OH)—
CH$_2$SO$_3^-$Na$^+$ VES-based treatment fluids according to the present invention show wide applicability in wellbore applications. The fluids may be used as, for example, fracturing fluids, selective acidising fluids, water shut-off fluids, well clean-out fluids, diversion fluids for acid and scale dissolver treatments. VES-based treatment fluids of the present invention are particularly useful as fracturing fluids.

VES-based treatment fluids of the present invention may be prepared by mixing the appropriate viscoelastic surfactant or mixture of viscoelastic surfactants with an aqueous solution (in practice, the mixwater that is available at the rigsite) with or without the addition of salt as determined by the composition of the available mixwater. The appropriate viscoelastic surfactant will normally be added in the form of a concentrated liquid with high surfactant activity; such surfactant concentrates are normally composed of the surfactant liquefied in an appropriate alcohol with/without water. In some embodiments, the VES-based treatment fluid may also contain other additives such as the proppant added to VES-based fracturing fluids.

As discussed above, the surfactants of the present invention show advantages over the surfactants known from the prior art. Various of these advantages are demonstrated in the accompanying figures. Thus, FIG. 1 demonstrates that the surfactant N-oleyl N-methyl taurate can form viscous fluids in a wide range of pH conditions, from strongly acid to strongly alkaline conditions and that these fluids maintain their high viscosity (>100 cP at 100 s$^{-1}$) at temperatures from room temperature up to the range 180-240° F. In the case of the data presented in FIG. 1, the surfactant product is Adinol

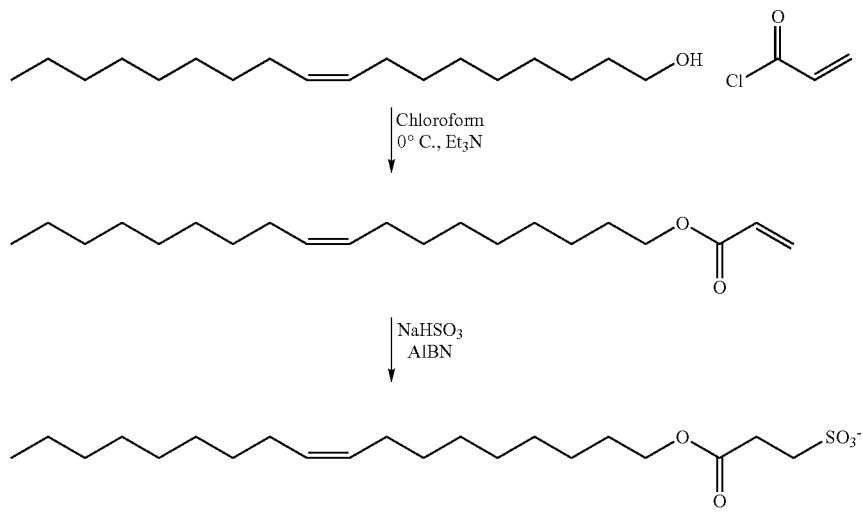

Compounds of formula VII can be prepared for example by the reaction of a fatty alcohol, epichlorohydrin and sodium sulphite; this reaction has been described in several patents such as U.S. Pat. No. 2,098,203 (assignee: Rohm and Hass)

OT64 available from Croda Oleochemicals, Goole, England, the product being present at 6 wt % (equivalent to 3.84 wt % active N-oleyl N-methyl taurate) with 6 wt % sodium chloride added to all three fluids.

Figure 3:
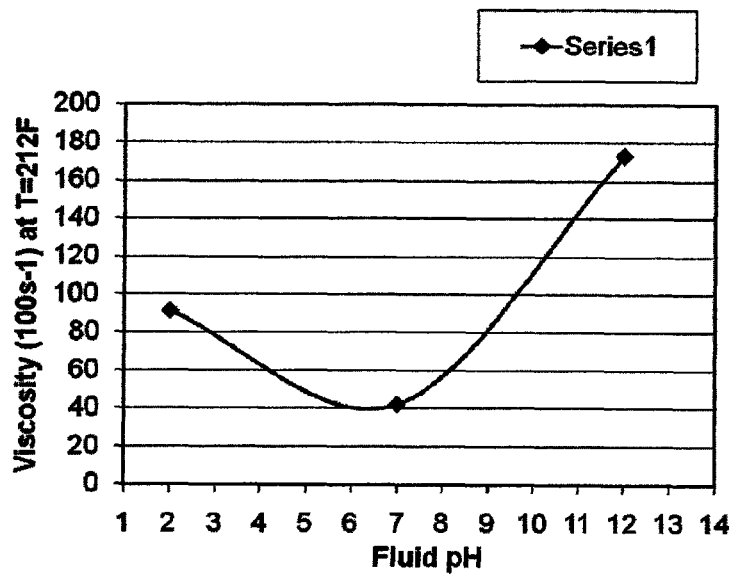
FIG. 3: shows, schematically, the effect of fluid pH on viscosity: it is possible to formulate a strongly acidic or strongly alkaline viscoelastic fluid which subsequently loses its viscosity as the fluid pH is neutralised either by increasing the pH or decreasing the pH using additives within the fluid or by interaction of the acidic or alkaline fluid with formation brine during backflow.
Figure 4:
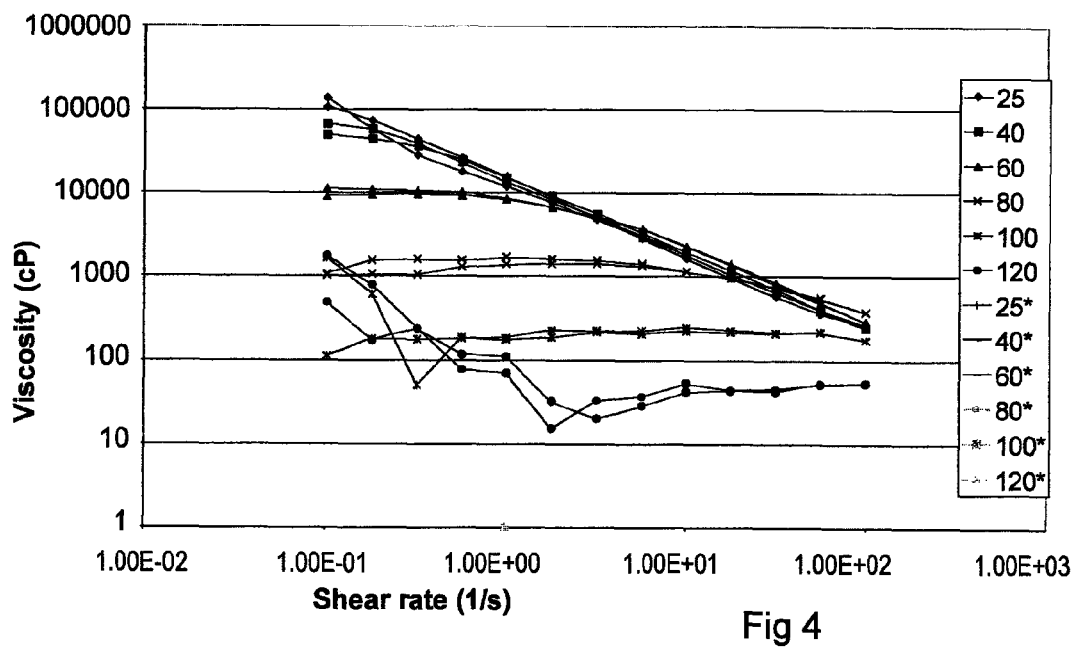
FIG. 4: illustrates the rheology of a viscoelastic gel based on N-oleyl N-methyl taurate. The surfactant product is Hostapon TPHC available from Clairant GmbH, Surfactant Division, Frankfurt, Germany.

From FIG. 1, we observe that it is possible to formulate a strongly acidic or strongly alkaline visco-elastic fluid. The data illustrated in FIG. 3 show that the viscoelastic fluid tested in FIG. 1 subsequently loses its viscosity as the fluid pH is neutralized either by increasing the pH or decreasing the pH using additives within the fluid or by interaction of the acidic or alkaline fluid with formation brine during backflow.

A key advantage of using viscoelastic gels based on the sulphonate surfactants hereinabove described is their tolerance to the presence of divalent cations such as calcium ions. Typically, N-oleyl N-methyl taurate gels can tolerate at least 4000 mg/L $Ca^{++}$ (added as calcium chloride) compared to around 400 mg/L for gels based on oleyl amide succinate or <400 mg/L for gels based on oleic acid.

Figure 5:
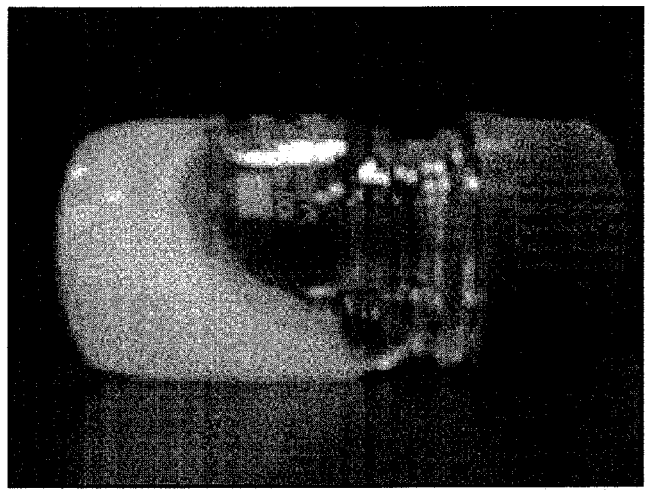
FIG. 5: shows the viscoelastic gel formed by N-oleyl N-methyl taurate on addition of calcium chloride without any coaddition of a monovalent alkali metal salt such as sodium chloride or potassium chloride.
Figure 6:
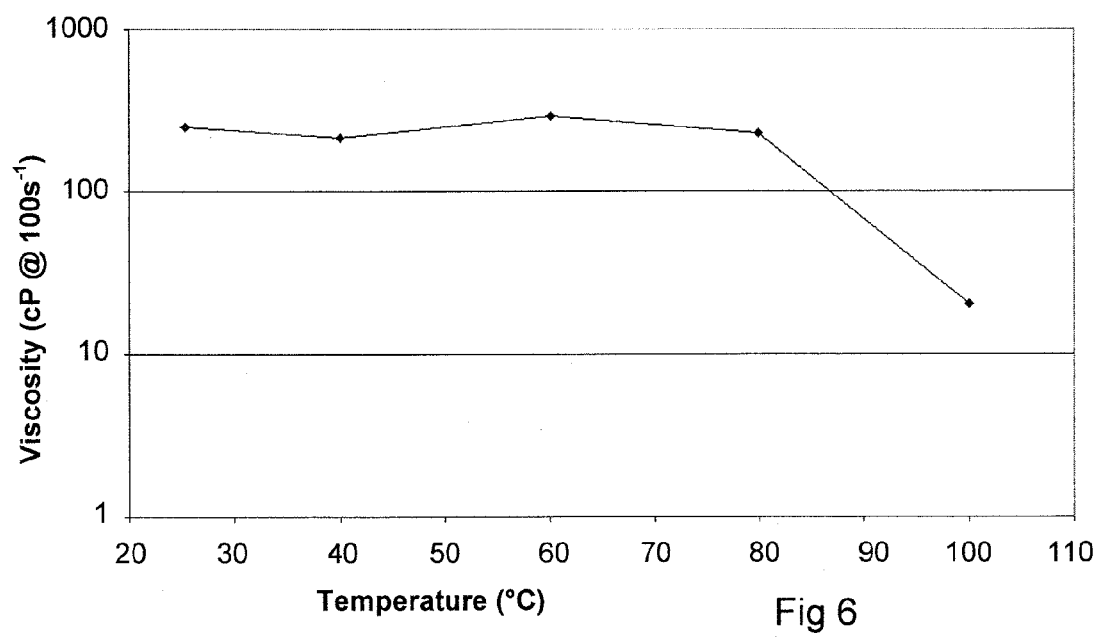
FIG. 6: illustrates that potassium chloride can be used in place of sodium chloride in the formation of a viscoelastic gel by N-oleyl N-methyl taurate.

FIG. 5 shows the viscoelastic gel formed by N-oleyl N-methyl taurate on addition of calcium chloride without any coaddition of a monovalent alkali metal salt such as sodium chloride or potassium chloride. FIG. 6 shows that potassium chloride in place of sodium chloride can also be used to form the viscoelastic gel. This advantage allows visco-elastic gels based on the hereinabove described anionic sulphonate surfactants and especially N-oleyl N-methyl taurate, to show tolerance to broad variability in the ionic composition of the mixwater, including seawater.

Figure 7:
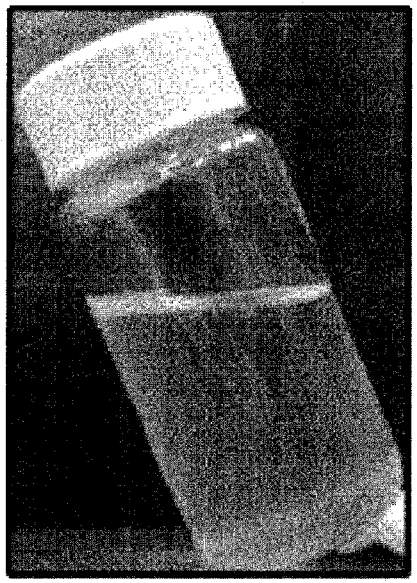
FIG. 7: shows that Adinol OT64 powder can be liquefied using a mixture of isopropanol and water, the result being a low viscosity liquid with product activity 40 wt % (25.6 wt % N-oleyl N-methyl taurate).

Typically, N-oleyl N-methyl taurate products are high activity solid powders although liquid paste products are also available. FIG. 7 shows that the Adinol OT64 powder can be liquified using a mixture of isopropanol and water, the result being a low viscosity liquid with product activity 40 wt % (25.6 wt % N-oleyl N-methyl taurate). This particular solution does not represent the highest surfactant activity that can be achieved and other solvent chemistries and combinations can be employed such as other alcohols, glycol ethers and polyglycol ethers.

Figure 8A:
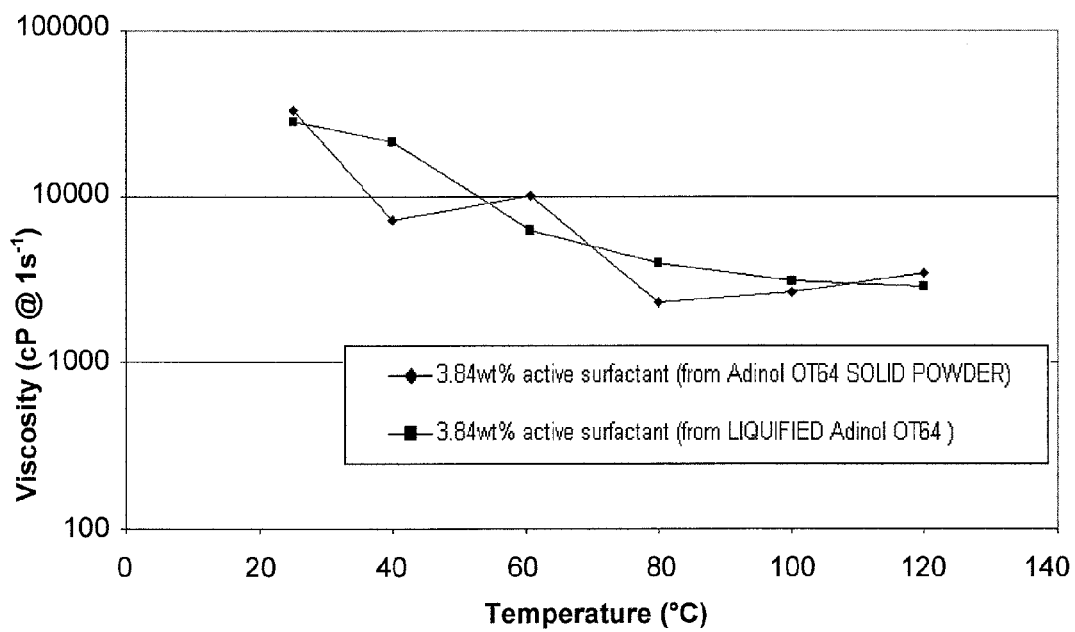
FIG. 8: demonstrates that there is little or no apparent reduction in the low or high shear viscosity of the viscoelastic gel prepared using either the liquid product of the powdered product.
Figure 8B:
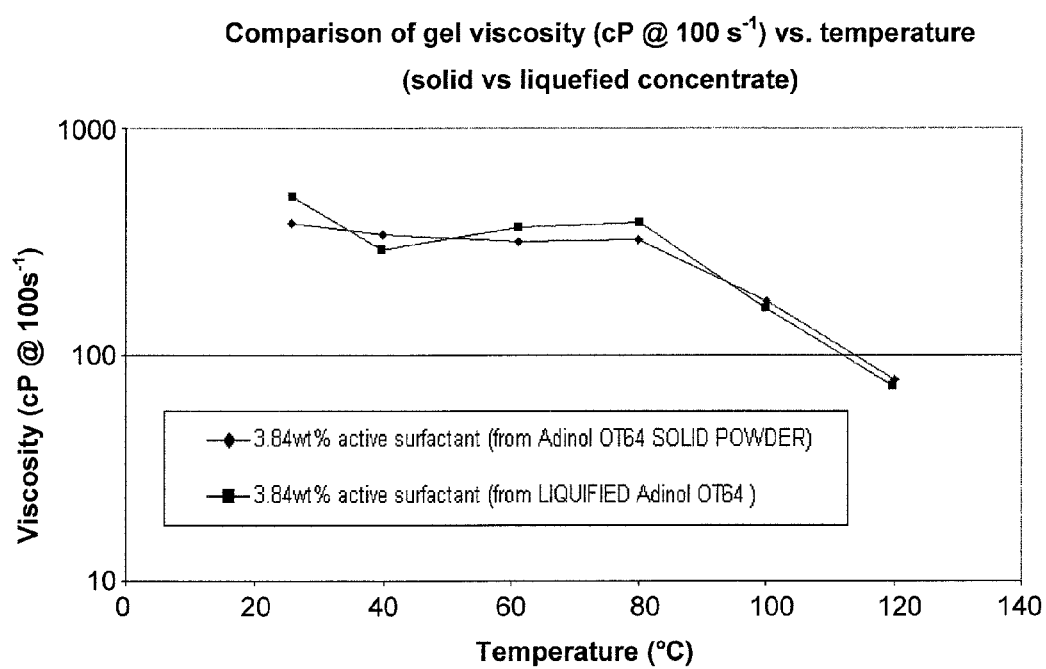

When the liquid product is used to prepare viscoelastic gels according to the invention there is little or no apparent reduction in the low or high shear viscosity of the gel compared to that achieved by preparing the same fluid using the powdered product (FIG. 8). An acidic, neutral or alkaline viscoelastic gel can be prepared from such a liquid concentrate of sodium N-oleyl N-methyl taurate.

Figure 9:
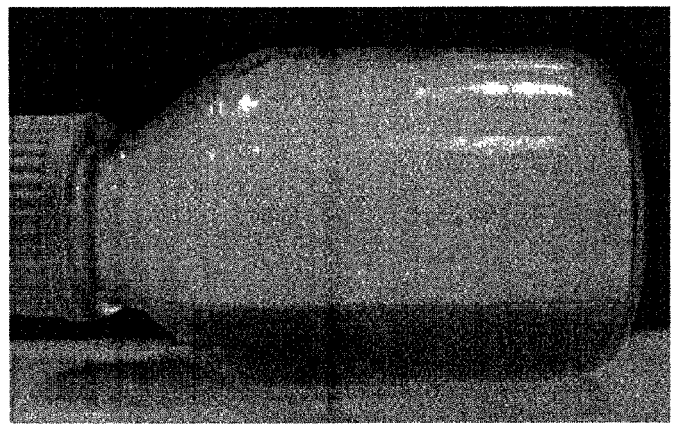
FIG. 9: shows that a stable foam is easily formed on vigorous shaking of an N-oleyl N-methyl taurate fluid at pH 3.5, thereby indicating that the foaming properties of the surfactant are maintained under low pH conditions such as those prevailing in a $CO_2$-foamed viscoelastic gel.
Figure 10:
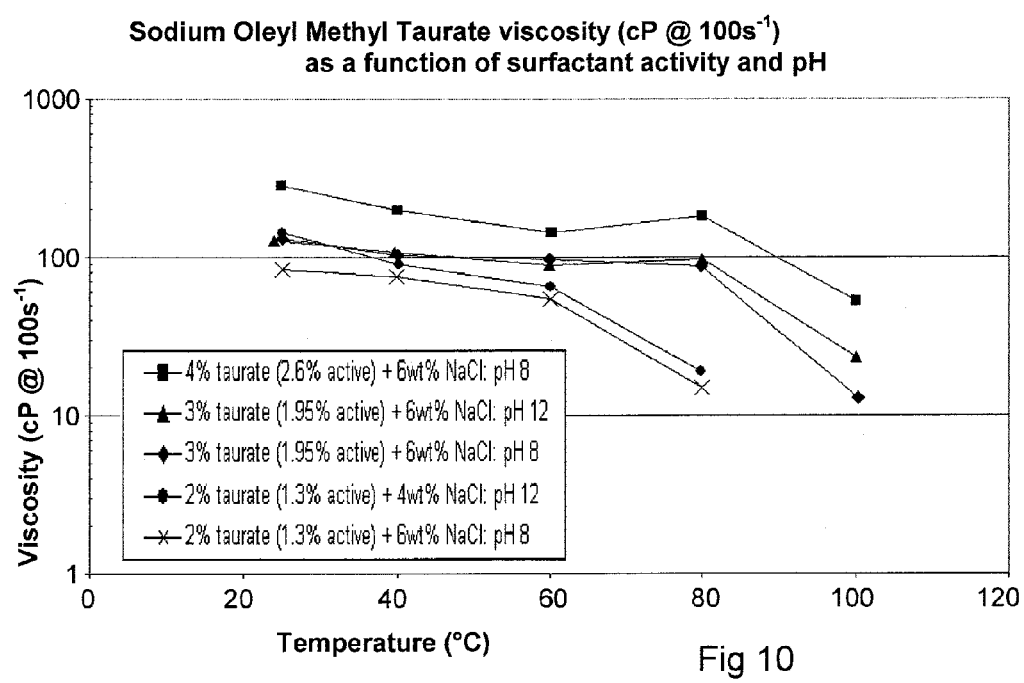
FIG. 10: shows that viscoelastic gels can be formulated using lower concentrations of N-oleyl N-methyl taurate and that the temperature tolerance of such gels decreases with decreasing surfactant concentration.

FIG. 9 shows that a stable foam is easily formed on vigorous shaking of a N-oleyl N-methyl taurate fluid at pH 3.5. This indicates that the foaming properties of the surfactant are maintained under low pH conditions such as those prevailing in a $CO_2$-foamed viscoelastic gel. By comparison this is not true for carboxylate surfactants of otherwise equivalent structure.

Figure 11:
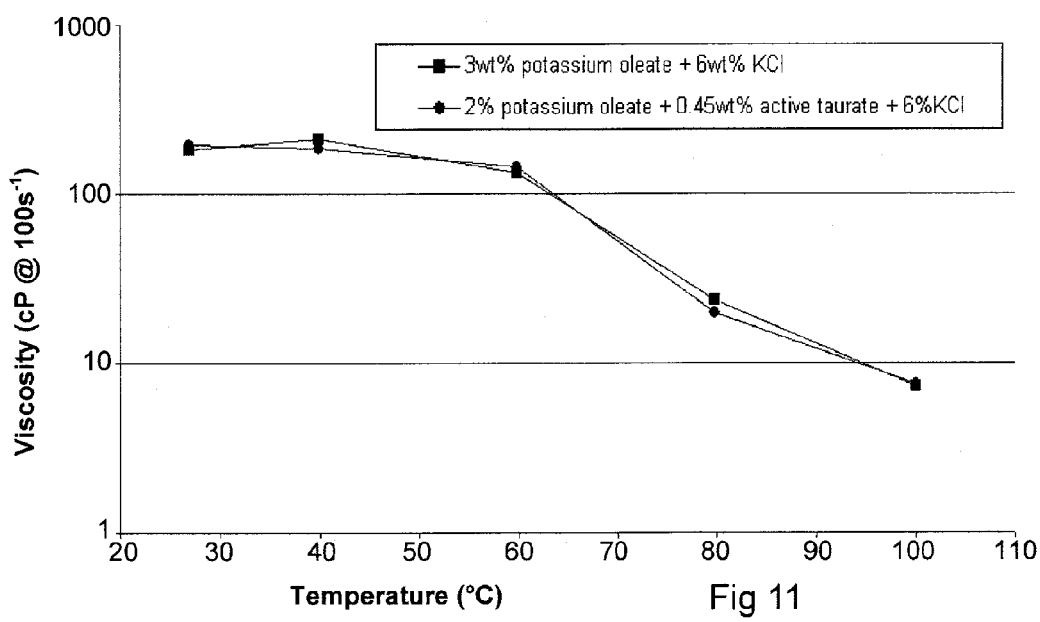
FIG. 11: shows the rheology of example formulations where the primary surfactant is N-oleyl N-methyl taurate in mixed surfactant systems containing a secondary surfactant. Mixed N-oleyl N-methyl taurate/potassium oleate gels can be formulated for use under alkaline conditions.
Figure 12:
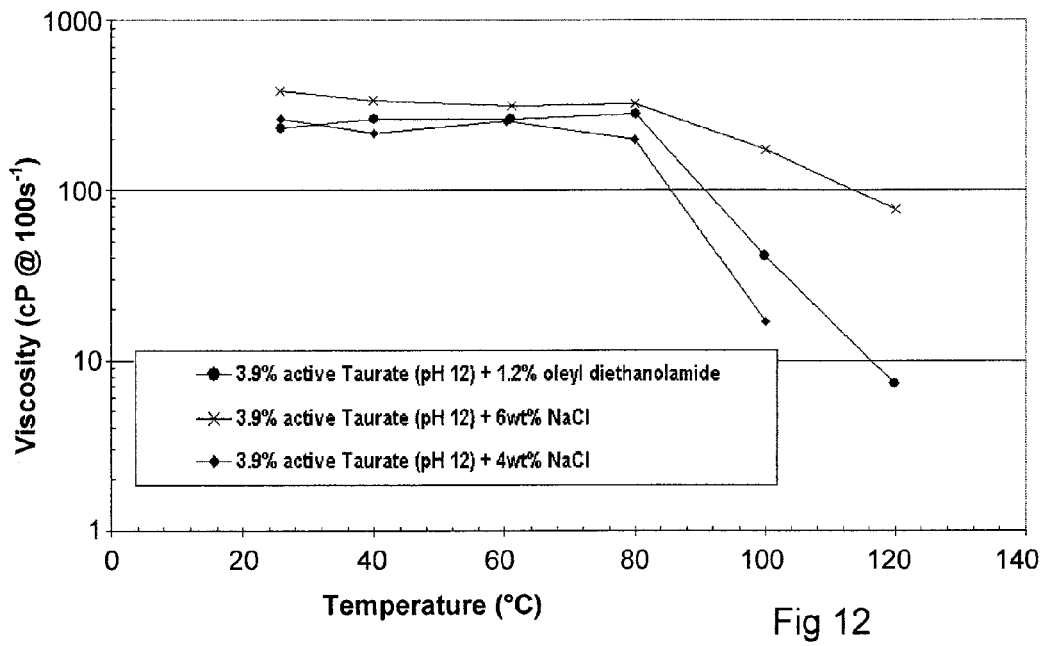
FIG. 12: shows that sodium N-oleyl N-methyl taurate can form a viscoelastic gel on addition of oleyl diethanolamide, in the absence of any added salt.
Figure 13:
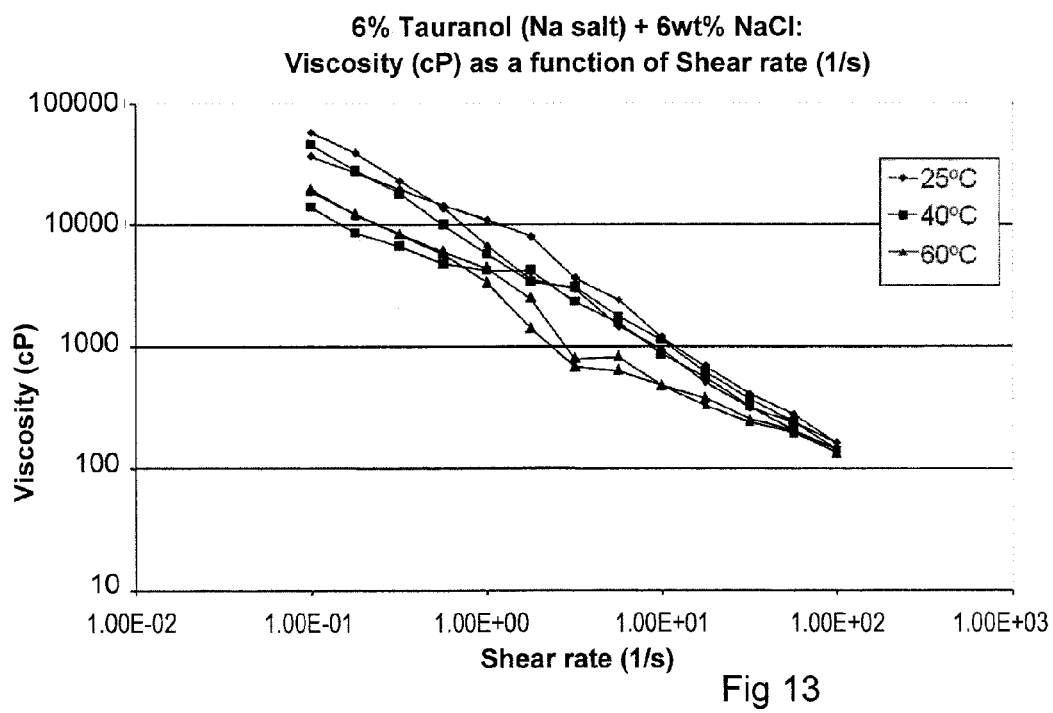
FIG. 13: shows the flow rheology of a gel formulation based on 6 wt % Tauranol (where the Tauranol product is a solution of 32-33 wt % sodium N-tallyl N-methyl taurate in an ispropanol/water mixture supplied by Finetex Inc., North Carolina, U.S.A.) and 6 wt % sodium chloride at pH 12 measured at 25, 40 and 60° C.
Figure 14:
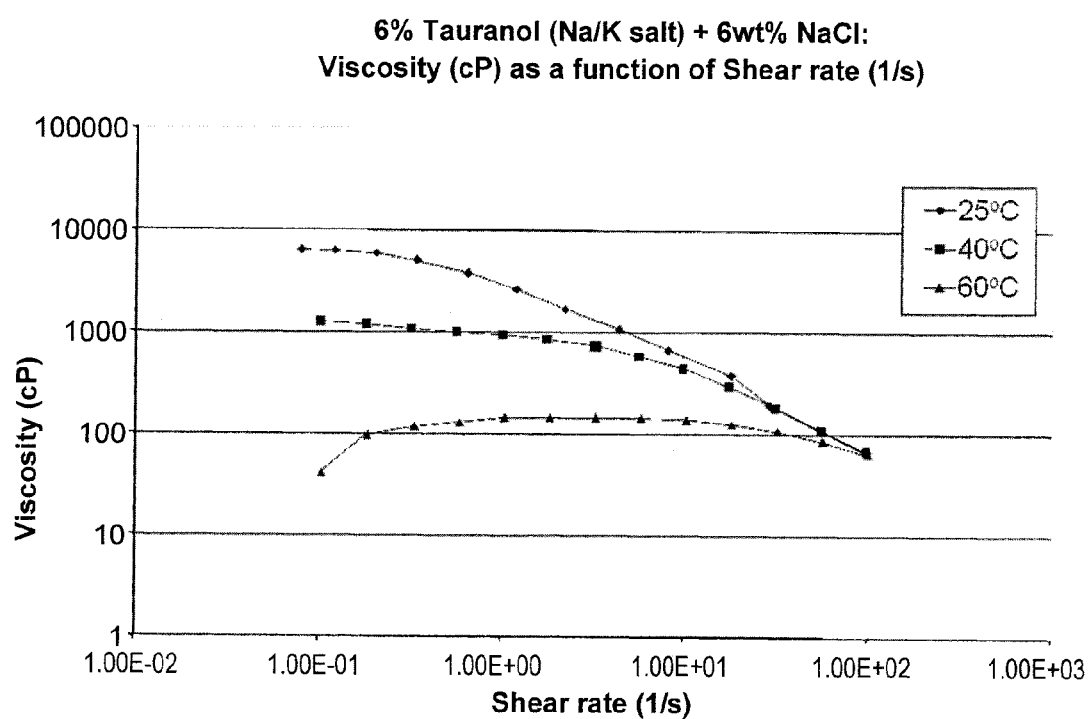
FIG. 14: shows the flow rheology of a gel formulation based on 6 wt % Tauranol (where the Tauranol product is a 28 wt % solution of a mixed potassium/sodium N-tallyl N-methyl taurate salt in water again supplied by Finetex Inc., North Carolina, U.S.A.) and 6 wt % sodium chloride at pH 12 measured at 25, 40 and 60° C.

FIGS. 11 and 12 show the rheology of example formulations where the primary surfactant is N-oleyl N-methyl taurate in mixed surfactant systems containing a secondary surfactant. FIG. 11 shows that mixed N-oleyl N-methyl taurate/potassium oleate gels can be formulated for use under alkaline conditions. FIG. 12 shows that sodium N-oleyl N-methyl taurate can form a viscoelastic gel on addition of oleyl diethanolamide, in the absence of any added salt.

The performance of VES surfactant systems according to the present invention have been assessed in terms of the rheology.

A controlled stress rheometer (Bohlin model type CVO-50) was used to measure the rheological properties of the solutions. Using a concentric cylinders (Couette) geometry (inner radius of the outer cylinder, $R_i$=1.375 cm, outer radius of the inner cylinder, $R_o$=1.25 cm, and inner cylinder length=3.78 cm), corresponding to the geometry of German DIN standard 53019, the viscosity of each gel was measured at a particular shear rate.

For the particular geometry of the rheometer, the shear rate was calculated as:

$$\dot{\gamma} = \frac{RPM \cdot 2\pi}{60} \frac{2 \cdot R_i^2 R_o^2}{\left(\frac{R_i + R_o}{2}\right)^2 (R_o^2 - R_i^2)},$$

where RPM is the rotational speed (in revolutions per minute) of the inner cylinder. The viscosity was then obtained for each measurement by dividing the measured stress by the calculated shear rate.

The invention claimed is:

1. An aqueous wellbore fluid comprising an anionic viscoelastic surfactant of formula I:

R—X—$(CR_5R_6)_m$—$SO_3^{-B+}$    (I)

in which:
R is a saturated or unsaturated, linear or branched aliphatic hydrocarbon chain comprising from 15 to 22 carbon atoms, including mixtures thereof and/or optionally incorporating an aryl group;
X is —(C=O)N($R_7$)— or —N($R_7$)(C=O)—;
$R_5$ and $R_6$ are the same or different and are each independently hydrogen, a linear saturated aliphatic hydrocarbon chain of at least 1 carbon atom, a branched saturated aliphatic hydrocarbon chain of at least 2 carbon atoms, or a linear saturated aliphatic hydrocarbon chain of at least 1 carbon atom or a branched aliphatic hydrocarbon chain of at least 2 carbon atoms with one or more of the hydrogen atoms replaced by a hydroxyl group; or
when X is —N($R_7$)(C=O)—, the group $(CR_5R_6)$ may include a $COO^-$ group;
$R_7$ is a hydrogen, a linear saturated aliphatic hydrocarbon chain of at least 1 carbon atom, a branched saturated aliphatic hydrocarbon chain of at least 2 carbon atoms, a linear saturated aliphatic hydrocarbon chain of at least 1 carbon atom or a branched saturated aliphatic hydrocarbon chain of at least 2 carbon atoms with one or more of the hydrogen atoms replaced by a hydroxyl group, or a cyclic hydrocarbon group;
$B^+$ is hydrogen or a monovalent cation and
m is an integer of from 1 to 4;
in the form of monomeric unit, a dimer or oligomer; the amount of the anionic viscoelastic surfactant which is present in the wellbore fluid being sufficient that the fluid is an aqueous viscoelastic gel.

2. The wellbore fluid of claim 1 wherein the hydrocarbon chain R is a chain of 16 to 22 carbon atoms.

3. The wellbore fluid of claim 1 wherein the hydrocarbon chain R is a chain of 18 to 22 carbon atoms.

4. The wellbore fluid of claim 1 wherein R is derived from palmitic acid, erucic acid, oleic acid, coconut oil acid, tallow acid, tall oil acid, soya oil acid or rapeseed oil acid.

5. The wellbore fluid of claim 1 wherein $R_5$ and $R_6$ are the same.

6. The wellbore fluid of claim 1 wherein $R_5$ and $R_6$ are each hydrogen, a linear $C_{1-6}$ alkyl group or a branched $C_{2-6}$ alkyl group.

7. The wellbore fluid of claim 6 wherein $R_5$ and $R_6$ are each hydrogen or a methyl or ethyl group.

8. The wellbore fluid of claim 1 wherein $R_7$ is hydrogen or a $C_{1-6}$ alkyl group or a $C_{1-6}$ alkyl group substituted with an aryl group.

9. The wellbore fluid of claim 8 wherein $R_7$ is hydrogen, methyl, ethyl, propyl, butyl or a $C_{1-6}$ alkyl group substituted with an aryl group.

10. The wellbore fluid of claim 9 wherein $R_7$ is hydrogen or methyl.

11. The wellbore fluid of claim 1 wherein m is 2 or 3.

12. The wellbore fluid of claim 1, wherein the anionic viscoelastic surfactant is of formula IIA:

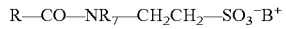
$$R-CO-NR_7-CH_2CH_2-SO_3^-B^+$$

wherein $B^+$, R and $R_7$ are as defined in claim 1, as a monomeric unit, dimer or oligomer.

13. The wellbore fluid of claim 12 in which the group R—CO— is selected from N-palmityl, N-erucyl, N-oleoyl, N-cocoyl, N-tallowyl, N-tallyl, N-soyayl and N-rapeseedyl and $R_7$ is hydrogen or a $C_{1-6}$ alkyl group.

14. The wellbore fluid of claim 1, wherein the anionic viscoelastic surfactant is of formula IIIA:

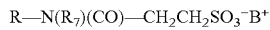
$$R-N(R_7)(CO)-CH_2CH_2SO_3^-B^+$$

in which $B^+$, R and $R_7$ are as defined in claim 1, as a monomeric unit, dimer or oligomer.

15. The wellbore fluid of claim 1, wherein the anionic viscoelastic surfactant is selected from an N-acyl taurate and an N-acyl N-methyl taurate.

16. The wellbore fluid of claim 15, wherein the anionic viscoelastic surfactant is selected from N-cetyl taurate, N-erucyl taurate, N-oleoyl taurate, N-cocoyl taurate, N-tallowyl taurate, N-tallyl taurate, N-soyayl taurate, N-rapeseedyl taurate. N-cetyl N-methyl taurate, N-erucyl N-methyl taurate, N-oleoyl N-methyl taurate, N-cocoyl N-methyl taurate, N-tallowyl N-methyl taurate, N-tallyl N-methyl taurate, N-soyayl N-methyl taurate and N-rapeseedyl N-methyl taurate.

17. The wellbore fluid of claim 1 being a fracturing fluid, selective acidising fluid, water shut-off fluid, well clean-out fluid or diversion fluid for acid and scale dissolver treatments.

18. A method of fracturing a subterranean formation, comprising the steps of:
(A) providing a wellbore fluid according to claim 1, and
(B) pumping the fluid through a wellbore and into a subterranean formation at a pressure sufficient to fracture the formation.

19. A method for the preparation of a viscoelastic gel treatment fluid comprising admixing an anionic viscoelastic surfactant as defined in claim 1 with an alcohol or amine additive.

20. The wellbore fluid of claim 1 which is an acidising fluid or a diversion fluid for acid treatments.

21. A wellbore service fluid comprising an aqueous viscoelastic surfactant having the structure of formula

$$R_1-X-(CR_5R_6)_m-A^{\ominus}B^{\oplus}$$

where (i) $R_1$ is a saturated or unsaturated, linear or branched aliphatic chain of at least 18 carbon atoms;
(ii) X is an $R_7N(CO)$, or $(CO)NR_7$ or —(C=O)O— or —O(C=O)—group;
(iii) m is at least one;
(iv) $R_5$, $R_6$ and $R_7$ are each independently hydrogen; a linear or branched, saturated aliphatic chain of at least 1 carbon atom; or a linear or branched, saturated aliphatic chain of at least 1 carbon atom with one or more of the hydrogen atoms replaced by a hydroxyl group,
(v) $A^{\ominus}$ is a sulfonate anionic group; and
(vi) $B^{\oplus}$ is hydrogen or a monovalent cation;
the amount of the anionic viscoelastic surfactant which is present in the wellbore fluid being sufficient that the fluid is an aqueous viscoelastic gel.

22. The method of claim 21 wherein $R_5$ and $R_6$ are both hydrogen.

23. The wellbore fluid of claim 21 which is an acidising fluid or a diversion fluid for acid treatments.

24. A method for preparing a wellbore fluid which is predominantly aqueous comprising:
admixing an anionic viscoelastic surfactant of formula I:

$$R-X-(CR_5R_6)_m-SO_3^-B^+ \quad (I)$$

in which:
R is a saturated or unsaturated, linear or branched aliphatic hydrocarbon chain comprising from 18 to 22 carbon atoms, including mixtures thereof and/or optionally incorporating an aryl group
X is —(C=O)N($R_7$)—, —N($R_7$)(C=O)—, —N($R_7$)—, —(C=O)O— or —O(C=O)—;
$R_5$ and $R_6$ are the same or different and are each independently hydrogen, a linear saturated aliphatic hydrocarbon chain of at least 1 carbon atom, a branched saturated aliphatic hydrocarbon chain of at least 2 carbon atoms, or a linear saturated aliphatic hydrocarbon chain of at least 1 carbon atom or a branched aliphatic hydrocarbon chain of at least 2 carbon atoms with one or more of the hydrogen atoms replaced by a hydroxyl group; or
when X is —N($R_7$)(C=O)— or —O(C=O)—, the group ($CR_5R_6$) may include a $COO^-$ group;
$R_7$ is a hydrogen, a linear saturated aliphatic hydrocarbon chain of at least 1 carbon atom, a branched saturated aliphatic hydrocarbon chain of at least 2 carbon atoms, a linear saturated aliphatic hydrocarbon chain of at least 1 carbon atom or a branched saturated aliphatic hydrocarbon chain of at least 2 carbon atoms with one or more of the hydrogen atoms replaced by a hydroxyl group, or a cyclic hydrocarbon group;
$B^+$ is hydrogen or a monovalent cation and
m is an integer of from 1 to 4;
in the form of monomeric unit, a dimer or oligomer;
with an alcohol or amine additive to form a liquid concentrate and thereafter mixing that concentrate with water to form the wellbore fluid, the amount of the anionic viscoelastic surfactant which is present in the wellbore fluid being sufficient that the fluid is a viscoelastic gel.

25. The method of claim 24 wherein R is derived from palmitic acid, erucic acid, oleic acid, coconut oil acid, tallow acid, tall oil acid, soya oil acid or rapeseed oil acid.

26. The method of claim 24, wherein the anionic viscoelastic surfactant is selected from the group consisting of:

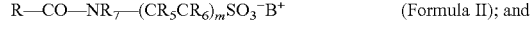
$$R-CO-NR_7-(CR_5CR_6)_m SO_3^-B^+ \quad \text{(Formula II); and}$$

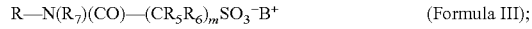
$$R-N(R_7)(CO)-(CR_5R_6)_m SO_3^-B^+ \quad \text{(Formula III);}$$

with R, $R_5$, $R_6$, $R_7$, $B^+$ and m as defined in claim 24, as a monomeric unit, a dimer or oligomer.

27. The method of claim 26 wherein $R_5$ and $R_6$ are each hydrogen or a methyl or ethyl group.

28. The method of claim 24, wherein the anionic viscoelastic surfactant is of formula IIA:

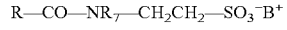
$$R-CO-NR_7-CH_2CH_2-SO_3^-B^+$$

wherein the group R—CO— is selected from N-palmityl, N-erucyl, N-oleoyl, N-cocoyl, N-tallowyl, N-tallyl, N-soyayl and N-rapeseedyl;
$R_7$ is hydrogen or a $C_{1-6}$ alkyl group; and
$B^+$ is as defined in claim 24,
as a monomeric unit, dimer or oligomer.

29. The method of claim 24, wherein the anionic viscoelastic surfactant is of formula IIIA:

$$R-N(R_7)(CO)-CH_2CH_2SO_3^- B^+$$

in which $B^+$, R and $R_7$ are as defined in claim 24, as a monomeric unit, dimer or oligomer.

30. The method of claim 24, wherein the anionic viscoelastic surfactant is selected from an N-acyl taurate and an N-acyl N-methyl taurate.

31. The method of claim 24, wherein the anionic viscoelastic surfactant is selected from N-cetyl taurate, N-erucyl taurate, N-oleoyl taurate, N-cocoyl taurate, N-tallowyl taurate, N-tallyl taurate, N-soyayl taurate, N-rapeseedyl taurate, N-cetyl N-methyl taurate, N-erucyl N-methyl taurate, N-oleoyl N-methyl taurate, N-cocoyl N-methyl taurate, N-tallowyl N-methyl taurate, N-tallyl N-methyl taurate, N-soyayl N-methyl taurate and N-rapeseedyl N-methyl taurate.

* * * * *